US012727818B2

(12) United States Patent
Xu et al.

(10) Patent No.: US 12,727,818 B2
(45) Date of Patent: Sep. 8, 2026

(54) METHOD OF DETECTING LIVING TISSUE ELEMENT, DEVICE OF DETECTING LIVING TISSUE ELEMENT, AND WEARABLE APPARATUS

(71) Applicant: SUNRISE TECHNOLOGIES CO., LTD., Beijing (CN)

(72) Inventors: Kexin Xu, Beijing (CN); Tongshuai Han, Beijing (CN); Di Sun, Beijing (CN); Xueyu Liu, Beijing (CN)

(73) Assignee: SUNRISE TECHNOLOGIES CO., LTD., Beijing (CN)

( * ) Notice: Subject to any disclaimer, the term of this patent is extended or adjusted under 35 U.S.C. 154(b) by 371 days.

(21) Appl. No.: 18/264,980

(22) PCT Filed: Dec. 31, 2021

(86) PCT No.: PCT/CN2021/143507

§ 371 (c)(1),
(2) Date: Aug. 10, 2023

(87) PCT Pub. No.: WO2022/170880

PCT Pub. Date: Aug. 18, 2022

(65) Prior Publication Data

US 2024/0130676 A1 Apr. 25, 2024

(30) Foreign Application Priority Data

Feb. 11, 2021 (CN) ......................... 202110185765.7

(51) Int. Cl.
*A61B 5/00* (2006.01)
*A61B 5/02* (2006.01)

(52) U.S. Cl.
CPC .......... *A61B 5/4869* (2013.01); *A61B 5/0075* (2013.01); *A61B 5/02007* (2013.01); *A61B 5/6801* (2013.01); *A61B 5/7214* (2013.01)

(58) Field of Classification Search
CPC .............. A61B 5/1455; A61B 5/14551; A61B 5/14552; A61B 5/14556; A61B 5/14558
See application file for complete search history.

(56) References Cited

U.S. PATENT DOCUMENTS 5,452,717 A * 9/1995 Branigan ........... A61B 5/14552 600/323
5,515,847 A 5/1996 Braig et al.
(Continued)

FOREIGN PATENT DOCUMENTS

CA 3122875 * 6/2020 ............. A61B 5/681
CA 3122875 A1 * 6/2020 ............. A61B 5/681
(Continued)

OTHER PUBLICATIONS

Supplemental European Search Report for corresponding European Application No. 21925525.4, dated Dec. 9, 2024, 12 pages.
(Continued)

*Primary Examiner* — Robert L Nasser
(74) *Attorney, Agent, or Firm* — Westman, Champlin & Koehler, P.A.

(57) ABSTRACT

A method and a device of detecting a living tissue element and a wearable apparatus are provided. The method includes: irradiating a detection region with incident light, where the incident light passes through the detection region to form exit light exited from at least one exit position; obtaining a light intensity value corresponding to each beam of the exit light acquired by M photosensitive surfaces, to obtain T output light intensities, where each output light intensity is obtained by processing the light intensity value of the exit light acquired by one or more photosensitive surfaces, and each photosensitive surface is used to acquire the light intensity value of the exit light exited from the exit position within a predetermined anti-jitter range corresponding to the photosensitive surface, 1≤T≤M; and determining
(Continued)

a concentration of at least one detected tissue element according to at least one output light intensity.

29 Claims, 15 Drawing Sheets

(56) References Cited

U.S. PATENT DOCUMENTS

| | | | | |
|---|---|---|---|---|
| 5,655,530 | A * | 8/1997 | Messerschmidt .. | A61B 5/14532 600/366 |
| 5,676,142 | A | 10/1997 | Miwa et al. | |
| 6,091,487 | A | 7/2000 | Jackson et al. | |
| 7,101,365 | B1 | 9/2006 | Sharon | |
| 7,333,186 | B2 | 2/2008 | Oshima et al. | |
| 11,158,757 | B2 | 10/2021 | Lin et al. | |
| 2005/0209514 | A1 | 9/2005 | Oshima et al. | |
| 2007/0197886 | A1 | 8/2007 | Naganuma et al. | |
| 2010/0331636 | A1* | 12/2010 | Hubner ................ | A61B 5/1455 600/310 |
| 2011/0230739 | A1* | 9/2011 | Gretz ................... | G01N 33/582 600/344 |
| 2015/0038955 | A1 | 2/2015 | Bragagna et al. | |
| 2016/0242682 | A1 | 8/2016 | Gulati et al. | |
| 2016/0249836 | A1 | 9/2016 | Gulati et al. | |
| 2016/0313244 | A1 | 10/2016 | Shiono | |
| 2017/0164878 | A1 | 6/2017 | Connor | |
| 2017/0340252 | A1* | 11/2017 | Kiguchi ............... | A61B 5/6814 |
| 2018/0279965 | A1 | 10/2018 | Pandit et al. | |
| 2019/0015027 | A1 | 1/2019 | Xu | |
| 2020/0168757 | A1 | 5/2020 | Lin et al. | |
| 2021/0093237 | A1* | 4/2021 | Venugopal ............ | H10F 55/255 |
| 2022/0054051 | A1 | 2/2022 | Xu et al. | |
| 2022/0059717 | A1 | 2/2022 | Lin et al. | |

FOREIGN PATENT DOCUMENTS

| | | | |
|---|---|---|---|
| CN | 1669526 | A | 9/2005 |
| CN | 103826529 | A | 5/2014 |
| CN | 108814620 | A | 11/2018 |
| CN | 111214209 | A | 6/2020 |
| CN | 111317442 | A | 6/2020 |
| CN | 111317443 | A | 6/2020 |
| CN | 111514469 | A | 8/2020 |
| GB | 2357844 | A | 7/2001 |
| JP | 2004267613 | A | 9/2004 |
| JP | 2011110085 | A | 6/2011 |
| JP | 2016206175 | A | 12/2016 |
| JP | 2016537069 | A | 12/2016 |
| KR | 10-2020-0072865 | A | 6/2020 |
| WO | 2018151150 | A1 | 1/2020 |
| WO | 2020119825 | A1 | 6/2020 |

OTHER PUBLICATIONS

Machine generated translation of the First Office Action regarding corresponding Japanese Patent Application No. 2023-548642, dated Jul. 23, 2024, filed Nov. 20, 2023, 5 pages.

The First Office Action regarding corresponding Japanese Patent Application No. 2023-548642, dated Jul. 23, 2024, filed Nov. 20, 2023, 5 pages.

Translation of Office Action regarding corresponding Korean application No. 10-2023-7030941, dated May 30, 2025, 27 pages.

International Search Report and Written Opinion from International Application No. PCT/CN2021/143507, dated Mar. 23, 2022.

First Office Action, including Search Report, for Chinese Patent Application No. 202110185765.7, dated Aug. 11, 2022, 26 pages.

Translation of Korean Office Action for Korean Patent Application No. KR 10-2023-7030941, dated Aug. 22, 2025, 21 pages.

Evgeniya Kirilina et al. “Identifying and quantifying main components of physiological noise in functional near infrared spectroscopy on the prefrontal cortex”, Frontiers in Human Neuroscience, vol. 7, Article 864, Dec. 17, 2013 , 17 pages.

* cited by examiner

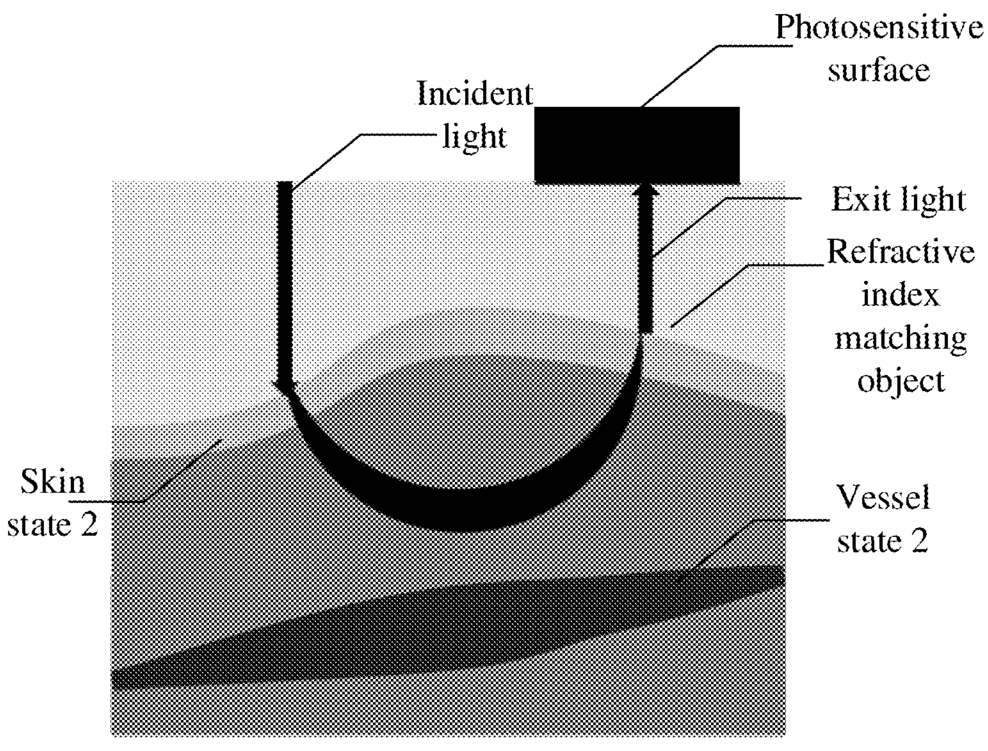
FIG. 29
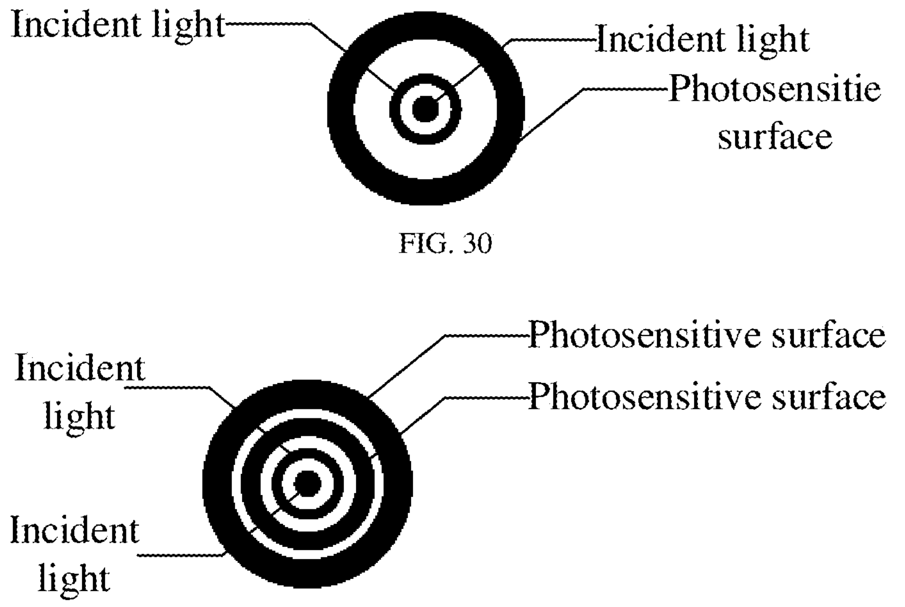
FIG. 30
FIG. 31

METHOD OF DETECTING LIVING TISSUE ELEMENT, DEVICE OF DETECTING LIVING TISSUE ELEMENT, AND WEARABLE APPARATUS

CROSS-REFERENCE TO RELATED APPLICATION(S)

This application is a Section 371 National Stage Application of International Application No. PCT/CN2021/143507, filed on Dec. 31, 2021, entitled "METHOD OF DETECTING LIVING TISSUE ELEMENT, DEVICE OF DETECTING LIVING TISSUE ELEMENT, AND WEARABLE APPARATUS", which published as WIPO Publication No. WO 2022/170880 A1, on Aug. 18, 2022, which claims priority to Chinese Application No. 202110185765.7, filed on Feb. 11, 2021, the contents of which are hereby incorporated by reference in their entireties.

TECHNICAL FIELD

Embodiments of the present disclosure relate to a field of spectrum detection technology, and in particular, to a method of detecting a living tissue element, a device of detecting a living tissue element, and a wearable apparatus.

BACKGROUND

A variety of tissue elements, such as blood glucose, fat, and white blood cells, etc. are contained in a body fluid of a human body. A concentration of each tissue element is required to be within a corresponding concentration range to ensure a healthy operation of the human body. However, for some individuals, the tissue element is prone to imbalance, that is, the concentration of the tissue element is not within a numerical range, which may lead to diseases, and endanger health and even life. For such objects, there is a need to perform a real-time detection on the tissue element.

An optical method has characteristics of rapidness, non-invasiveness, and multidimensional information, etc., and is generally adopted to detect a tissue element in a related art. According to a detection principle, the optical method mainly includes Raman spectrometry, polarization method, optical coherence tomography method, photo-acoustic spectrometry, mid-infrared spectrometry and near-infrared spectrometry.

In a process of implementing concepts of the present disclosure, the inventors found that the related art has at least a problem that a detection accuracy is not high in the related art.

SUMMARY

In view of this, embodiments of the present disclosure provide a method of detecting a living tissue element, a device of detecting a living tissue element, and a wearable apparatus.

In an aspect of embodiments of the present disclosure, a method of detecting a living tissue element is provided, including: irradiating a detection region with incident light having at least one predetermined wavelength, where the incident light passes through the detection region to form at least one beam of exit light exited from at least one exit position, and the incident light is incident on at least two incident positions; obtaining a light intensity value corresponding to each beam of the exit light acquired by M photosensitive surfaces, so as to obtain T output light intensities, where each of the T output light intensities is obtained by processing the light intensity value of the exit light acquired by one or more of the M photosensitive surfaces, and each of the M photosensitive surfaces is configured to acquire the light intensity value of the exit light exited from the exit position within a predetermined anti-jitter range corresponding to the photosensitive surface, 1≤T≤M; and determining a concentration of at least one detected tissue element according to at least one output light intensity corresponding to the at least one predetermined wavelength.

In another aspect of embodiments of the present disclosure, a device of detecting a living tissue element is provided, including: a light source module configured to irradiate a detection region by incident light having at least one predetermined wavelength, where the incident light passes through the detection region to form at least one beam of exit light exited from at least one exit position, and the incident light is incident on at least two incident positions; an acquisition module including M photosensitive surfaces, where each of the M photosensitive surfaces is configured to acquire the light intensity value of the exit light exited from the exit position within a predetermined anti-jitter range corresponding to the photosensitive surface, the acquisition module is configured to obtain a light intensity value corresponding to each beam of the exit light acquired by the M photosensitive surfaces, so as to obtain T output light intensities, and each of the T output light intensities is obtained by processing the light intensity value of the exit light acquired by one or more of the M photosensitive surfaces; and a processing module configured to determine a concentration of at least one detected tissue element according to at least one output light intensity corresponding to the at least one predetermined wavelength.

In another aspect of embodiments of the present disclosure, a wearable apparatus is provided, and the apparatus includes the device of detecting the living tissue element as described above.

BRIEF DESCRIPTION OF THE DRAWINGS

The above and other objectives, features and advantages of the present disclosure will be clearer with following descriptions of embodiments of the present disclosure with reference to the accompanying drawings, in which:

FIG. 29 schematically shows another schematic diagram of a photosensitive surface receiving exit light in a case of a refractive index matching object being filled according to embodiments of the present disclosure;

FIG. 30 schematically shows a schematic diagram of an incidence by circular incident light and ring incident light and a peripheral reception by a ring photosensitive surface according to embodiments of the present disclosure;

FIG. 31 schematically shows a schematic diagram of an incidence by circular incident light and ring incident light and a peripheral reception by a first set of photosensitive surfaces according to embodiments of the present disclosure;

DETAILED DESCRIPTION OF EMBODIMENTS

Figures 1, 2:
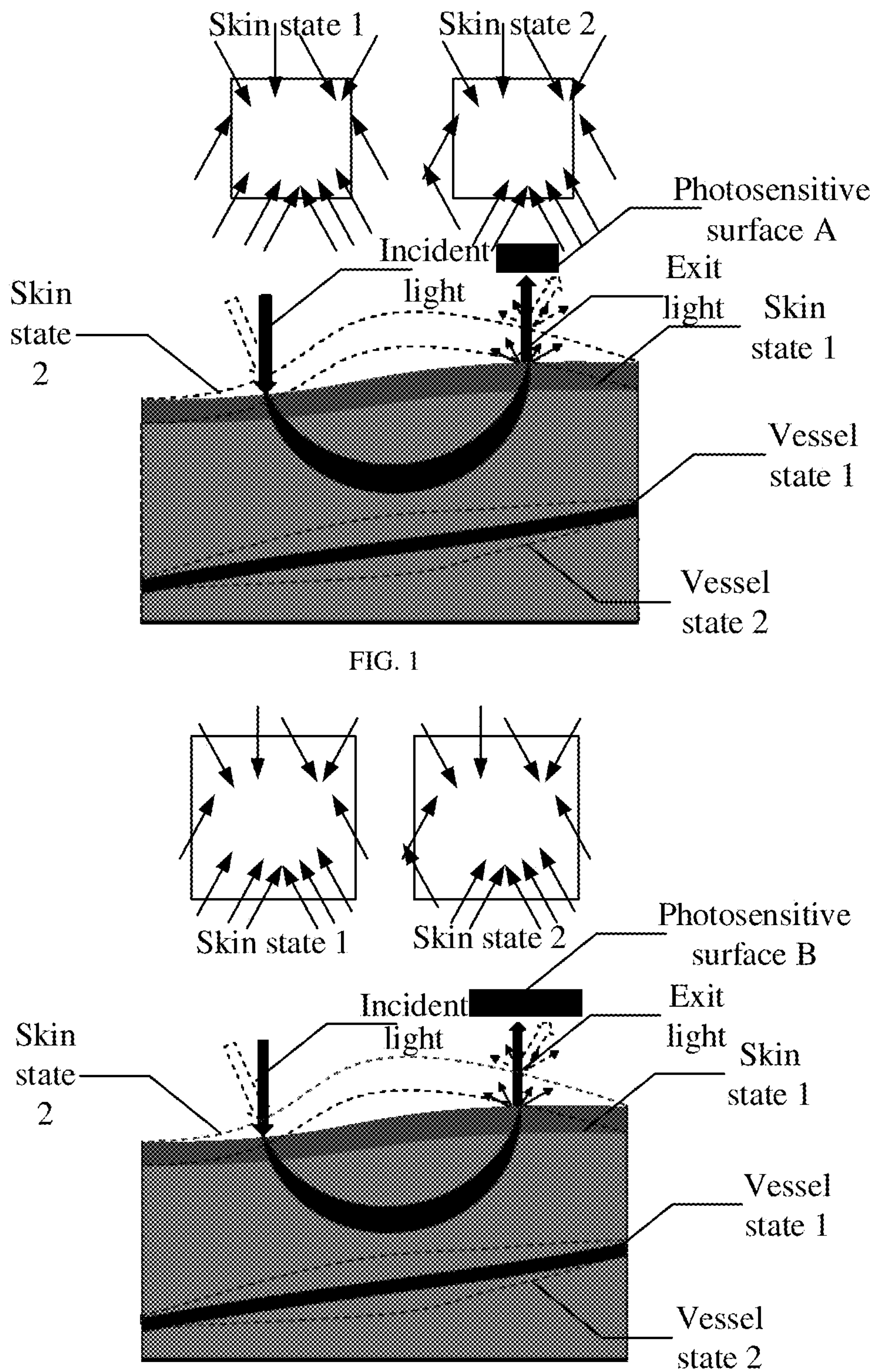
FIG. 1 schematically shows a schematic diagram of receiving exit light using a photosensitive surface with a small area when a jitter occurs according to embodiments of the present disclosure.
FIG. 2 schematically shows a schematic diagram of receiving exit light using a photosensitive surface with a large area when a jitter occurs according to embodiments of the present disclosure.

Embodiments of the present disclosure will be described below with reference to the accompanying drawings. It should be understood, however, that these descriptions are merely exemplary and are not intended to limit the scope of the present disclosure. In the following detailed descriptions, for ease of interpretation, many specific details are set forth to provide a comprehensive understanding of embodiments of the present disclosure. However, it is clear that one or more embodiments may also be implemented without these specific details. In addition, in the following descriptions, descriptions of well-known structures and technologies are omitted to avoid unnecessarily obscuring concepts of the present disclosure.

Terms used herein are for the purpose of describing specific embodiments only and are not intended to limit the present disclosure. The terms "including", "containing", etc. used herein indicate the presence of the feature, step, operation and/or component, but do not exclude the presence or addition of one or more other features, steps, operations or components.

All terms used herein (including technical and scientific terms) have the meanings generally understood by those skilled in the art, unless otherwise defined. It should be noted that the terms used herein shall be interpreted to have meanings consistent with the context of this specification, and shall not be interpreted in an idealized or overly rigid manner.

In a case of using the expression similar to "at least one selected from A, B, and C", it should be explained according to the meaning of the expression generally understood by those skilled in the art (for example, "a system including at least one selected from A, B, and C" should include but not be limited to a system including A alone, a system including B alone, a system including C alone, a system including A and B, a system including A and C, a system including B and C, and/or a system including A, B and C). In a case of using the expression similar to "at least one selected from A, B, or C", it should be explained according to the meaning of the expression generally understood by those skilled in the art (for example, "a system including at least one selected from A, B, or C" should include but not be limited to a system including A alone, a system including B alone, a system including C alone, a system including A and B, a system including A and C, a system including B and C, and/or a system including A, B and C).

A research on a living tissue element detection based on an optical method has experienced nearly fifty years of development, and a large number of scientific research institutes and companies have invested great research enthusiasm in this field. Due to a weak absorption of a detected tissue element and a small variation range of a concentration of the detected tissue element of the detected living object, a signal of the detected tissue element is generally weak and may be easily affected by interference such as a change in a detection condition. The weak signal of the detected tissue element may be easily submerged by the above-mentioned interference. Up to now, there has not appeared a solution that may achieve a reliable tissue element detection. Therefore, the living tissue element detection is a global problem that needs to be solved. The tissue element may include blood glucose, fat, and white blood cells, etc. The signal of the detected tissue element represents a change in an output light intensity caused by a change in a concentration of the detected tissue element. The detection condition may be understood as a condition that affects a transmission path of light. The detection condition may include a controllable detection condition and an uncontrollable detection condition. The controllable detection condition refers to a detection condition that may be controlled within a predetermined change range (that is, kept unchanged or substantially unchanged) by adopting an effective control method during each tissue element detection process. The effective control method may be implemented with a hardware design. The uncontrollable detection condition refers to a detection condition with unpredictable and uncontrollable characteristics. The controllable detection condition may include a temperature, a pressure, a detection region and a detection posture, etc. The uncontrollable detection condition may include a change in a physiological background and a drift of a detection device, etc.

In a process of implementing concepts of the present disclosure, the inventors found that main causes for the low detection accuracy obtained by using the related art are as follows.

The inventors found that: different detection results may be obtained if only an intensity distribution of a light spot irradiated with incident light on a detection region is changed while other conditions remain unchanged; and if a detection result obtained when arranging a photosensitive surface close to a blood vessel is compared with a detection result obtained when arranging the same photosensitive surface far away from the blood vessel while keeping other conditions unchanged, the detection result obtained when arranging the photosensitive surface far away from the blood vessel is better than that obtained when arranging the photosensitive surface close to the blood vessel. The detection result may be represented by a relative variation of a light intensity value of exit light received by the photosensitive surface or a standard deviation of the light intensity value. The less the relative variation of the light intensity value, the better the detection result, and the less the standard deviation of the light intensity value, the better the detection result. When studying the causes for the different detection results, it was found that changing the intensity distribution of the light spot irradiated with the incident light on the detection region may represent a randomness of an irradiation of a light source, and a distance to the blood vessel may represent a strength of a pulse beat. The randomness of the irradiation of the light source and the pulse beat are both sources of jitter. Therefore, it has been found that one of the causes for the low detection accuracy is the jitter.

On the basis of a research on the jitter, it was found that a source of the jitter may be classified into an internal source and an external source. The internal source may further include a change in the physiological background in addition to the pulse beat. The external source may further include an uncertainty of a transmission of the incident light in addition to the randomness of the irradiation of the light source. The randomness of the irradiation of the light source may be reflected by the intensity distribution of the light spot irradiated with the incident light on the detection region. It was found that both the jitter caused by the internal source and the jitter caused by the external source may affect a transmission path of light in the tissue, and then affect the intensity distribution of the exit light on the detection region.

In order to solve the problem of the low detection accuracy caused by the jitter, the inventors found that a solution of acquiring the light intensity value of the exit light by using a photosensitive surface with a large area (that is, a large-area photosensitive surface) may be adopted to effectively reduce an adverse influence of the jitter on the detection result. That is, the large-area photosensitive surface may effectively reduce the adverse influence caused by the jitter. The so-called "large-area photosensitive surface" may be understood as a photosensitive surface with such area that the photosensitive surface may acquire the light intensity value of the exit light exited from an exit position within a predetermined anti-jitter range. The area of the large-area photosensitive surface is continuous. The large-area photosensitive surface is made of a photosensitive material, and it is different from a single-point optical fiber reception and a joint reception of multiple single optical fibers. A description will be given below to explain in detail why the solution of acquiring the output light intensity of the exit light by using the large-area photosensitive surface may be adopted to effectively reduce the adverse influence of the jitter on the detection result.

In the large-area photosensitive surface, a ratio of an area of the photosensitive surface that may stably receive the exit light to the area of the photosensitive surface may be increased, so that a stability of receiving the exit light may be improved, an adverse influence of a change in the intensity distribution of the exit light caused by the jitter may be reduced, and then the detection accuracy may be improved. The stability may be represented by a relative variation of the light intensity value of the exit light received by the photosensitive surface or a standard deviation of the light intensity value. The less the relative variation of the light intensity value, the higher the stability, and the less the standard deviation of the light intensity value, the higher the stability.

Illustratively, the jitter caused by the pulse beat is taken as an example for description. The pulse beat may be reflected by a blood vessel state. FIG. 1 schematically shows a schematic diagram of receiving the exit light using a photosensitive surface with a small area when a jitter occurs according to embodiments of the present disclosure. FIG. 2 schematically shows a schematic diagram of receiving the exit light using a photosensitive surface with a large area when a jitter occurs according to embodiments of the present disclosure. The jitter occurs in FIG. 1 is the same as that occurs in FIG. 2. An area of a photosensitive surface A in FIG. 1 is smaller than an area of a photosensitive surface B in FIG. 2. Both the photosensitive surface A and the photosensitive surface B are square photosensitive surfaces. In FIG. 1 and FIG. 2, a blood vessel state 1 represents a vasoconstriction state, a blood vessel state 2 represents a vasodilation state, a skin state 1 represents a skin state corresponding to the blood vessel state 1, and a skin state 2 represents a skin state corresponding to the blood vessel state 2. A change from the skin state 1 to the skin state 2 reflects a jitter.

The detection results obtained using photosensitive surfaces with different areas when the same jitter occurs are compared. The detection result is represented by the relative variation of the light intensity value of the exit light received by the photosensitive surface within a predetermined time period or the standard deviation of the light intensity value. The relative variation of the light intensity value may be determined by: calculating a difference between a maximum light intensity value and a minimum light intensity value within the predetermined time period, calculating an average value of the light intensity values within the predetermined time period, calculating a ratio of the difference to the average value, and determining the ratio as the relative variation of the light intensity value. The predetermined time period may be a pulsation cycle.

The detection results also show that the detection result obtained by using the photosensitive surface B is better than the detection result obtained by using the photosensitive surface A whether the detection result is represented by the relative variation of the light intensity value of the exit light received by the photosensitive surface or the detection result is represented by the standard deviation of the light intensity value of the exit light received by the photosensitive surface.

As the area of the photosensitive surface B is larger than the area of the photosensitive surface A, it may indicate that the large-area photosensitive surface may improve the stability of receiving the exit light, and then reduce the adverse influence of the change in the intensity distribution of the exit light caused by the jitter, thereby improving a detection accuracy.

In addition, the output light intensity of the exit light is weak, the change in the output light intensity caused by a change in the concentration of the detected tissue element is also weak, and the method of receiving the exit light adopted in the related art has a low efficiency of receiving the exit light, so that the received output light intensity has a low signal-to-noise ratio, which results in a low detection accuracy. The large-area photosensitive surface of embodiments of the present disclosure may improve the signal-to-noise ratio of the output light intensity, thereby improving the detection accuracy. This is because the large-area photosensitive surface may receive a wide range of exit light and improve the efficiency of receiving the exit light, so that the signal-to-noise ratio of the output light intensity may be increased, and the detection accuracy may be improved.

It should be noted that the large-area photosensitive surface described in embodiments of the present disclosure may achieve a high stability and efficiency of receiving the exit light in a case of a small distance to a surface of the detection region, that is, in a case that the large-area photosensitive surface is close to the surface of the detection region. This may not be achieved by using a single-point optical fiber reception and a joint reception of multiple single optical fibers due to a constraint of a numerical aperture of the optical fiber and a limitation of a state change of the optical fiber. The state of the optical fiber is easily affected by an environment, and the state change of the optical fiber has a great influence on the stability of receiving the exit light.

It should also be noted that the large-area photosensitive surface is generally adopted to improve the signal-to-noise ratio of the output light intensity. In other words, a function of the large-area photosensitive surface is generally to increase the signal-to-noise ratio of the output light intensity, which is different from a main function of the large-area photosensitive surface in embodiments of the present disclosure. In embodiments of the present disclosure, the main function of the large-area photosensitive surface is to effectively suppress the jitter. A description will be given below in conjunction with specific embodiments.

Figure 3:
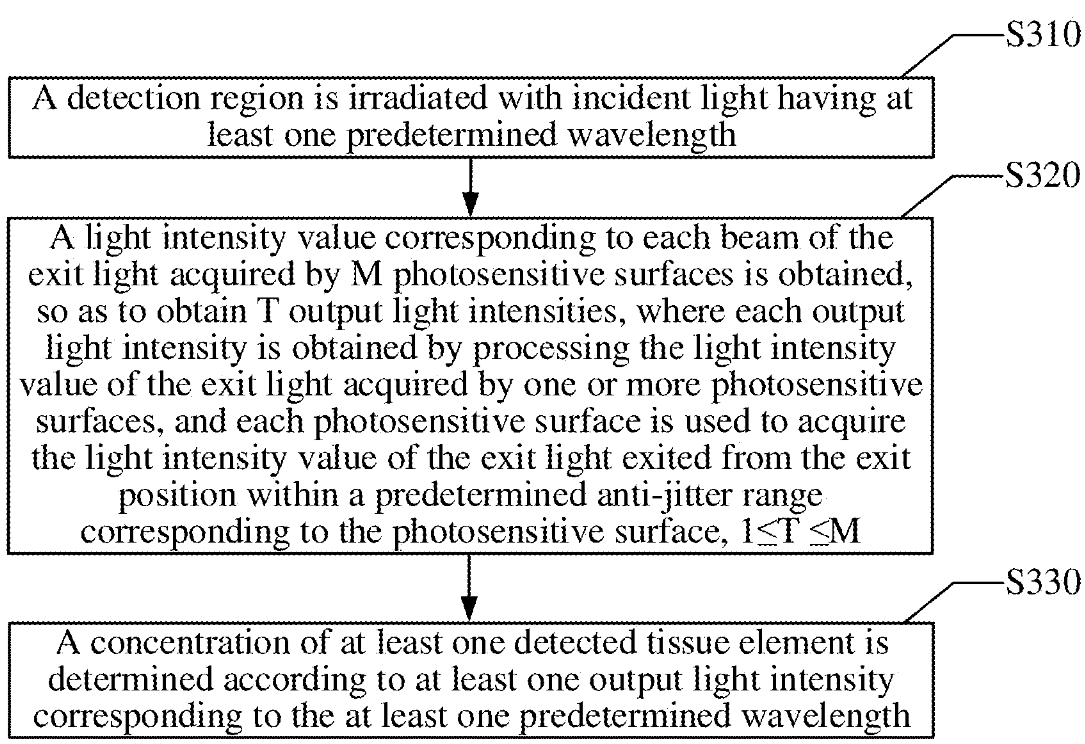
FIG. 3 schematically shows a flowchart of a method of detecting a living tissue element according to embodiments of the present disclosure.

FIG. 3 schematically shows a flowchart of a method of detecting a living tissue element according to embodiments of the present disclosure.

As shown in FIG. 3, the method includes operations S310 to S330.

In operation S310, a detection region is irradiated with incident light having at least one predetermined wavelength.

The incident light passes through the detection region to form at least one beam of exit light exited from at least one exit position, and the incident light is incident on at least two incident positions.

According to embodiments of the present disclosure, as different detection sites have different skin characteristics, including smoothness, hair presence or absence, flatness, skin thickness and softness, etc., it is needed to select an appropriate detection site according to an actual situation, such as a structure of a detection probe. The detection site may include at least one selected from a finger, a palm, an arm, a forehead, or an earlobe. The detection region may be a region on the detection site.

According to embodiments of the present disclosure, the predetermined wavelength may be a wavelength sensitive to the detected tissue element. A band to which the predetermined wavelength belongs may include an ultraviolet band, a visible light band, a near-infrared band, a mid-infrared band or a far-infrared band. Exemplarily, if the detected tissue element is blood glucose, the predetermined wavelength may be a wavelength sensitive to blood glucose accordingly, which may be specifically 1550 nm or 1609 nm. The incident light may be collimated or non-collimated. There may be at least two incident positions of the incident light.

In operation S320, a light intensity value corresponding to each beam of the exit light acquired by M photosensitive surfaces is obtained, so as to obtain T output light intensities. Each output light intensity is obtained by processing the light intensity value of the exit light acquired by one or more photosensitive surfaces, and each photosensitive surface is used to acquire the light intensity value of the exit light exited from the exit position within a predetermined anti-jitter range corresponding to the photosensitive surface. $1 \leq T \leq M$.

According to embodiments of the present disclosure, in order to improve the detection accuracy, it is needed to ensure that each photosensitive surface may acquire the light intensity value of the exit light exited from the exit position within the predetermined anti-jitter range corresponding to the photosensitive surface, which requires the area of the photosensitive surface to be as large as possible. Each photosensitive surface has a corresponding predetermined anti-jitter range, and different photosensitive surfaces correspond to the same or different predetermined anti-jitter ranges. A description will be given below from three aspects with examples to illustrate that the larger the area of the photosensitive surface, the better the effect of suppressing the jitter. In the examples, the area of the photosensitive surface A is smaller than the area of the photosensitive surface B, and both the photosensitive surface A and the photosensitive surface B are square photosensitive surfaces.

In a first aspect, a jitter caused by a pulse beat may be suppressed. The photosensitive surface A and the photosensitive surface B are respectively arranged at a same position on the detection region, which is a position close to the blood vessel. A detection result obtained by using the photosensitive surface A may be compared with a detection result obtained by using the photosensitive surface B when other conditions are the same. The detection result is represented by a relative variation of the light intensity value of the exit light received by the photosensitive surface within a pulsation cycle or a standard deviation of the light intensity value. The method of calculating the relative variation of the light intensity value is as described above, and will not be repeated here. It was found that the relative variation of the light intensity value of the exit light received by the photosensitive surface B is less than the relative variation of the light intensity value of the exit light received by the photosensitive surface A, and the standard deviation of the light intensity value of the exit light received by the photosensitive surface B is less than the standard deviation of the light intensity value of the exit light received by the photosensitive surface A. Therefore, it may be concluded that the detection result obtained by using the photosensitive surface B is better than the detection result obtained by using the photosensitive surface A whether the detection result is represented by the relative variation of the light intensity value of the exit light received by the photosensitive surface or the detection result is represented by the standard deviation of the light intensity value of the exit light received by the photosensitive surface.

Since the detection result obtained by using the photosensitive surface B is better than the detection result obtained by using the photosensitive surface A, and the area of the photosensitive surface B is larger than the area of the photosensitive surface A, it may indicate that the larger the area of the photosensitive surface, the better the effect of suppressing the jitter caused by the pulse beat.

In a second aspect, a jitter caused by a change in the intensity distribution of the light spot irradiated with the incident light on the detection region may be suppressed. The intensity distribution of the light spot irradiated with the incident light on the detection region may be changed while other conditions remain unchanged. The detection result obtained by using the photosensitive surface A may be compared with the detection result obtained by using the photosensitive surface B. The detection result is represented by a relative variation of the light intensity value of the exit light received by the photosensitive surface within a predetermined period or a standard deviation of the light intensity value. The method of calculating the relative variation of the light intensity value is as described above, and will not be repeated here. It was found that the relative variation of the light intensity value of the exit light received by the photosensitive surface B is less than the relative variation of the light intensity value of the exit light received by the photosensitive surface A, and the standard deviation of the light intensity value of the exit light received by the photosensitive surface B is less than the standard deviation of the light intensity value of the exit light received by the photosensitive surface A. Therefore, it may be concluded that the detection result obtained by using the photosensitive surface B is better than the detection result obtained by using the photosensitive surface A whether the detection result is represented by the relative variation of the light intensity value of the exit light received by the photosensitive surface or the detection result is represented by the standard deviation of the light intensity value of the exit light received by the photosensitive surface.

Since the detection result obtained by using the photosensitive surface B is better than the detection result obtained by using the photosensitive surface A, and the area of the photosensitive surface B is larger than the area of the photosensitive surface A, it may indicate that the larger the area of the photosensitive surface, the better the effect of suppressing the jitter caused by the change in the intensity distribution of the light spot irradiated with the incident light on the detection region.

Figure 4:
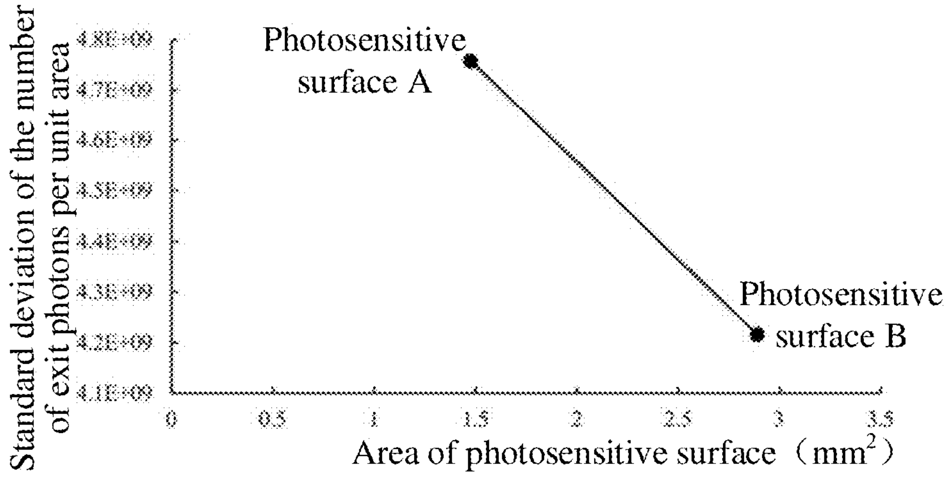
FIG. 4 schematically shows a schematic diagram of a detection result obtained based on a Monte Carlo simulation method according to embodiments of the present disclosure.

In a third aspect, a jitter caused by an uncertainty of the transmission of the incident light may be suppressed. A Monte Carlo simulation method is used, where a central incidence is performed using incident light with a photon number of $10^{15}$, the photosensitive surface A and the photosensitive surface B are respectively arranged at a distance of 2.4 mm from the center of the incident light, and the simulation is performed twenty-two times. The detection result obtained by using the photosensitive surface A may be compared with the detection result obtained by using the photosensitive surface B. The detection result is represented by a standard deviation of a number of exit photons per unit area. The less the standard deviation of the number of exit photons per unit area, the better the suppression effect. FIG. 4 schematically shows a schematic diagram of the detection result obtained based on the Monte Carlo simulation method according to embodiments of the present disclosure. It was found that the standard deviation of the number of exit photons per unit area corresponding to the photosensitive surface B is less than the standard deviation of the number of exit photons per unit area corresponding to the photosensitive surface A. That is, the detection result obtained by using the photosensitive surface B is better than the detection result obtained by using the photosensitive surface A.

Since the detection result obtained by using the photosensitive surface B is better than the detection result obtained by using the photosensitive surface A, and the area of the photosensitive surface B is larger than the area of the photosensitive surface A, it may indicate that the larger the area of the photosensitive surface, the better the effect of suppressing the jitter caused by the uncertainty of the transmission of the incident light.

Through the examples from the above three aspects, it may indicate that the larger the area of the photosensitive surface, the better the effect of suppressing the adverse influence of the jitter on the detection result.

According to embodiments of the present disclosure, each photosensitive surface may be provided as a ring photosensitive surface or a non-ring photosensitive surface. The non-ring photosensitive surface may include a sector-ring photosensitive surface, a circular photosensitive surface, a sector photosensitive surface, an elliptical photosensitive surface, or a polygon photosensitive surface. The polygonal photosensitive surface may include a square photosensitive surface, a rectangular photosensitive surface, or a triangular photosensitive surface.

According to embodiments of the present disclosure, each of the M photosensitive surfaces may be used separately, partially in combination, or all in combination. Used in combination means outputting one output light intensity. In embodiments of the present disclosure, a photosensitive surface for outputting one output light intensity is referred to as a homogeneous photosensitive surface. The homogeneous photosensitive surface may include one or more photosensitive surfaces. A condition for using different photosensitive surfaces in combination may be that for each photosensitive surface, an average optical path of the exit light received by the photosensitive surface is within an average optical path range. The average optical path range may be a range that is greater than or equal to a first average optical path threshold and less than or equal to a second average optical path threshold. The first average optical path threshold and the second average optical path threshold may be determined according to an optical path mean value and an optical path change amplitude. The optical path mean value is a mean value calculated according to the average optical paths of the exit light received at the photosensitive positions of the homogeneous photosensitive surface. Exemplarily, if the optical path mean value is a, and the optical path change amplitude is ±30%, then the first average optical path threshold may be 0.7a, and the second average optical path threshold may be 1.3a.

The average optical path is explained as follows. A transmission path of light in a tissue may be expressed by an optical path and a penetration depth. The optical path is used to represent a total distance that light travels in the tissue, and the penetration depth is used to represent a maximum longitudinal distance that light may reach in the tissue. For a determined source-detection distance, the average optical path is used to represent an average value of the optical path of light in the tissue. A probability distribution function of the optical path may be understood as a function of the source-detection distance and a tissue optical parameter. The source-detection distance represents a radial distance between a center of the incident light and a center of the photosensitive surface. Accordingly, in terms of mathematical expressions, the average optical path may be understood as a function of the source-detection distance and the tissue optical parameter. The tissue optical parameter may include an absorption coefficient, a scattering coefficient, and an anisotropy factor. A factor affecting the average optical path may include the absorption coefficient, the scattering coefficient, the anisotropy factor, and the source-detection distance.

According to embodiments of the present disclosure, the homogeneous photosensitive surface may be a ring photosensitive surface or a non-ring photosensitive surface. The homogeneous photosensitive surface being a ring photosensitive surface may include that the homogeneous photosensitive surface includes one photosensitive surface, and the homogeneous photosensitive surface is an independent ring photosensitive surface; or the homogeneous photosensitive surface includes a plurality of photosensitive surfaces, and the homogeneous photosensitive surface is a ring photosensitive surface formed by combining the plurality of photosensitive surfaces. The homogeneous photosensitive surface being a non-ring photosensitive surface may include that the homogeneous photosensitive surface includes one photosensitive surface, and the homogeneous photosensitive surface is an independent non-ring photosensitive surface; or the homogeneous photosensitive surface includes a plurality of photosensitive surfaces, and the homogeneous photosensitive surface is a non-ring photosensitive surface formed by combining the plurality of photosensitive surfaces.

In operation S330, a concentration of at least one detected tissue element is determined according to at least one output light intensity corresponding to the at least one predetermined wavelength.

According to embodiments of the present disclosure, after at least one output light intensity corresponding to the at least one predetermined wavelength is obtained, for each detected tissue element, the at least one output light intensity corresponding to the at least one predetermined wavelength may be processed using an interference suppression method to determine the concentration of the detected tissue element. The interference suppression method may include a differential detection method. The differential detection method may include a temporal differential detection method, a position differential detection method, or a wavelength differential detection method. Alternatively, the at least one output light intensity may also be processed using a non-differential detection method to determine the concentration of the detected tissue element.

According to technical solutions of embodiments of the present disclosure, the photosensitive surface may acquire the light intensity value of the exit light exited from the exit position within the corresponding predetermined anti-jitter range. In the photosensitive surface with the above-mentioned characteristics, a ratio of the area that may stably receive the exit light to the area of the photosensitive surface is increased, so that the stability of receiving the exit light is improved, the adverse influence of the change in the intensity distribution of the exit light caused by the jitter is reduced, and the detection accuracy is improved.

According to embodiments of the present disclosure, a ratio of an average optical path of the exit light received by each photosensitive surface in a target tissue layer to a total optical path is greater than or equal to a ratio threshold. The total optical path is a total distance that the exit light travels in the detection region.

According to embodiments of the present disclosure, a tissue model of the detected living object is generally a layered structure, that is, it may be divided into one or more layers. Different tissue layers carry different information of the detected tissue element. In order to improve the detection accuracy, it is required to ensure that the transmission path of the exit light mainly passes through the tissue layer that carries a rich information of the detected tissue element. A target tissue layer may be understood as the tissue layer that carries a rich information of the detected tissue element, or the tissue layer that is a main source of the detected tissue element. In the following description, a human body is taken as an example of the detected living object, and blood glucose is taken as an example of the detected tissue element.

A skin tissue model of the human body may be understood as a three-layer model, including epidermis, dermis and subcutaneous fat layer from outside to inside. The epidermis contains a small amount of interstitial fluid, and does not contain plasma and lymph. The dermis contains a large amount of interstitial fluid, and further contains a large amount of plasma and a small amount of lymph due to the presence of abundant capillaries. The subcutaneous fat layer contains a small amount of cellular fluid, and contains a large amount of plasma and a small amount of lymph due to the presence of blood vessels such as veins and arteries. Therefore, different tissue layers carry different information of the detected tissue element.

Since the epidermis contains a small amount of interstitial fluid, it is not an appropriate source of the blood glucose information. Although the subcutaneous fat layer contains a large amount of plasma and a relatively small amount of interstitial fluid, it is still not an appropriate source of the blood glucose information due to a limitation of the penetration depth of the incident light. The dermis contains abundant capillaries and a large amount of interstitial fluid, and the incident light may easily reach the dermis. Therefore, the dermis may be used as a main source of the blood glucose information. Accordingly, the target tissue layer may be the dermis.

According to embodiments of the present disclosure, the average optical path of the exit light in each tissue layer may be determined according to the optical path and the penetration depth.

In order to ensure that the transmission path of the exit light mainly passes through the target tissue layer, it is required to ensure that a ratio of the average optical path of the exit light received by each photosensitive surface in the target tissue layer to the total optical path is greater than or equal to a ratio threshold. The total optical path may be a total distance that the exit light travels in the detection region, that is, a total distance of a path that the incident light travels from entering the detection region, travelling in the detection region, to reaching the exit position. The ratio threshold is related to the tissue optical parameter and the source-detection distance between the center of the photosensitive surface and the center of the incident light.

It should be noted that, since the ratio of the average optical path of the exit light received by the photosensitive surface in the target tissue layer to the total optical path is limited in embodiments of the present disclosure, the area of the photosensitive surface in embodiments of the present disclosure may not be overly large, and it is a large area in an area range.

According to embodiments of the present disclosure, the method may further include the following operations.

A total area of the homogeneous photosensitive surface is determined according to a tissue structure feature in the detection region. The homogeneous photosensitive surface includes one or more photosensitive surfaces, and the homogeneous photosensitive surface is used to output one output light intensity.

According to embodiments of the present disclosure, the total area of the homogeneous photosensitive surface may be determined according to the tissue structure feature in the detection region. The tissue structure feature may be understood as a structure feature of the detection region.

For example, when the detection region is a region where three blood vessels intersect, if the homogeneous photosensitive surface is arranged in the region where the three blood vessels intersect, the total area of the homogeneous photosensitive surface is limited to an area of the region where the three blood vessels intersect, that is, the total area of the homogeneous photosensitive surface needs to be determined according to the area of the region where the three blood vessels intersect.

For another example, when the detection region is a region where a finger is located, if the homogeneous photosensitive surface is arranged in the region where the finger is located, the total area of the homogeneous photosensitive surface is limited by an area of the region where the finger is located, that is, the total area of the homogeneous photosensitive surface needs to be determined according to the area of the region where the finger is located.

It should be noted that the area of the photosensitive surface in embodiments of the present disclosure may be determined according to the tissue structure feature, and an area that is determined according to the tissue structure feature may generally not be overly large. Therefore, the area of the photosensitive surface in embodiments of the present disclosure may not be overly large, and it is a large area in the area range.

According to embodiments of the present disclosure, a ratio of the area of each photosensitive surface to a circumference of the photosensitive surface is greater than or equal to a ratio threshold.

According to embodiments of the present disclosure, the reason why the influence of the jitter caused by the uncertainty of the transmission of the incident light, the randomness of the light source, the change in the physiological background and the pulse beat on the distribution of the exit light on the detection region may be reduced by maximizing the ratio of the area of the photosensitive surface to the circumference of the photosensitive surface so that the ratio is greater than or equal to a ratio threshold is as follows.

For ease of explanation, the photosensitive surface is divided into two portions, including an edge portion and a non-edge portion (or inner portion). Generally, the jitter mainly affects the exit light acquired by the edge portion, while the non-edge portion is less affected, that is, the non-edge portion may acquire the exit light relatively stably. From another perspective, when the jitter occurs, the intensity distribution of the exit light on the detection region may change slightly. The light intensity value of the exit light received by the edge portion may change greatly with the change in the intensity distribution of the exit light, but most of the exit light at the non-edge portion may be acquired by the photosensitive surface relatively stably, so that the light intensity value of the exit light received by the non-edge portion may remain relatively stable. Therefore, it is possible to maximize a ratio of an area corresponding to the non-edge portion to the area of the photosensitive surface in order to effectively suppress the adverse influence of the jitter on the detection result, and the larger the ratio, the better the effect of reducing the adverse influence. The edge portion may be represented by the circumference of the photosensitive surface, and the non-edge portion may be represented by the area of the photosensitive surface. Thus, the ratio of the area of the photosensitive surface to the circumference of the photosensitive surface is required to be as large as possible.

For example, a photosensitive surface 1 is a circular photosensitive surface, and a photosensitive surface 2 is a square photosensitive surface. In a case of a same circumference, since the area of the photosensitive surface 1 is larger than the area of the photosensitive surface 2, the ratio of the area of the photosensitive surface 1 to the circumference of the photosensitive surface 1 is greater than the ratio of the area of the photosensitive surface 2 to the circumference of the photosensitive surface 2. Therefore, the effect of the photosensitive surface 1 reducing the adverse influence is better than the effect of the photosensitive surface 2 reducing the adverse influence.

It should be noted that the description for the ratio of the area of the photosensitive surface to the circumference of the photosensitive surface being greater than or equal to the ratio threshold is given on the basis of meeting the condition that the area of the photosensitive surface is greater than or equal to the area threshold. For most shapes of photosensitive surfaces, if the ratio of the area of the photosensitive surface to the circumference of the photosensitive surface is greater than or equal to the ratio threshold, a size of the area of the photosensitive surface is actually limited, because for most shapes of figures, the ratio of the area to the circumference of the figure has a positive correlation with the size of the area, that is, the greater the ratio of the area to the circumference of the figure, the larger the area of the figure.

For example, in a case of a circle, an area of the circle is $\pi R^2$, and a ratio of the area to the circumference of the circle is R/2, where R represents a radius. The ratio of the area to the circumference of the circle is only related to the radius, and the size of the area of the circle is only related to the radius. Therefore, the ratio of the area to the circumference of the circle has a positive correlation with the size of the area. If the ratio of the area to the circumference of the circle is limited, the size of the area of the circle is also limited. For another example, in a case of a square, an area of the square is $a^2$, and a ratio of the area to the circumference of the square is a/4, where a represents a side length. The ratio of the area to the circumference of the square is only related to the side length, and the size of the area of the square is only related to the side length. Therefore, the ratio of the area to the circumference of the square has a positive correlation with the size of the area. If the ratio of the area to the circumference of the square is limited, the size of the area of the square is also limited.

According to embodiments of the present disclosure, the ratio threshold is greater than or equal to 0.04 mm.

According to embodiments of the present disclosure, the area of the photosensitive surface in the present disclosure is a relatively large area, that is, the area of the photosensitive surface is a large area within an area range. A description will be given below for this case.

First, the area of the photosensitive surface may not be too small. The large-area photosensitive surface in embodiments of the present disclosure refers to a photosensitive surface with such area that the photosensitive surface may acquire the light intensity value of the exit light exited from the exit position within the predetermined anti-jitter range. Therefore, the large-area photosensitive surface in embodiments of the present disclosure has a large area used to achieve anti-jitter. Furthermore, the ratio of the area of the photosensitive surface to the circumference of the photosensitive surface may be used to indicate that the area of the photosensitive surface allows the photosensitive surface to acquire the light intensity value of the exit light exited from the exit position within the predetermined anti-jitter range, and the ratio of the area to the circumference of the photosensitive surface generally has a positive correlation with the area of the photosensitive surface. Therefore, if the ratio of the area to the circumference of the photosensitive surface is greater than or equal to the ratio threshold, the size of the area of the photosensitive surface is also actually limited, that is, it is also limited that the area of the photosensitive surface may not be too small by limiting that the ratio of the area to the circumference of the photosensitive surface is greater than or equal to the ratio threshold.

Second, the area of the photosensitive surface may not be overly large. In embodiments of the present disclosure, it is required that the ratio of the average optical path of the exit light received by the photosensitive surface in the target tissue layer to the total optical path is greater than or equal to the ratio threshold, and/or the area of the photosensitive surface is determined according to the tissue structure feature, so that the area of the photosensitive surface may not be overly large.

Therefore, the area of the photosensitive surface in embodiments of the present disclosure is a relatively large area, that is, a large area within the area range.

In addition, there may be a case that the photosensitive surface has a large area and also has a large circumference, so that the ratio of the area of the photosensitive surface to the circumference of the photosensitive surface is small, that is, the ratio of the area of the photosensitive surface to the circumference of the photosensitive surface is less than the ratio threshold. Therefore, it is possible that a photosensitive surface having a large absolute area does not meet the anti-jitter requirement. There may also be a case that the photosensitive surface has a small area and a large circumference, so that the ratio of the area of the photosensitive surface to the circumference of the photosensitive surface is less than the ratio threshold. Therefore, a photosensitive area having a very small area may not meet the anti-jitter requirement.

According to embodiments of the present disclosure, the photosensitive surface is in contact or non-contact with a surface of the detection region.

According to embodiments of the present disclosure, a form of the tissue element detection may include a contact detection and a non-contact detection. The contact detection may be implemented to prevent interference light from being received by the photosensitive surface, thereby further improving the detection accuracy. The non-contact detection may be implemented to avoid an influence of an interference factor such as temperature and pressure on the detection result, thereby further improving the detection accuracy.

If the photosensitive surface is arranged in contact with the surface of the detection region, it may be considered that the form of the tissue element detection is the contact detection. If the photosensitive surface is arranged in non-contact with the surface of the detection region, it may be considered that the form of the tissue element detection is the non-contact detection.

According to embodiments of the present disclosure, a distance between the photosensitive surface and the surface of the detection region is less than or equal to a first distance threshold, and the efficiency of the photosensitive surface receiving the exit light is greater than or equal to an efficiency threshold.

According to embodiments of the present disclosure, since the photosensitive surface is made of a photosensitive material and has a continuous area, a wide range of light intensity values may be received, and the efficiency of receiving the exit light may be improved. Based on this, the efficiency of receiving the exit light may be greater than or equal to the efficiency threshold even when the photosensitive surface is close to the surface of the detection region, that is, when the distance between the photosensitive surface and the surface of the detection region is less than or equal to the first distance threshold.

According to embodiments of the present disclosure, determining the concentration of the at least one detected tissue element according to the at least one output light intensity corresponding to the at least one predetermined wavelength may include the following operations.

In a case of determining the concentration of each detected tissue element in the at least one detected tissue element, for each predetermined wavelength in the at least one predetermined wavelength, a first output light intensity and a second output light intensity are determined from at least two output light intensities corresponding to the predetermined wavelength. The concentration of the detected tissue element is determined according to the first output light intensity and the second output light intensity corresponding to each predetermined wavelength.

According to embodiments of the present disclosure, the average optical path of the exit light corresponding to the first output light intensity is different from the average optical path of the exit light corresponding to the second output light intensity. For each detected tissue element, the concentration of the detected tissue element may be determined according to the first output light intensity and the second output light intensity corresponding to each predetermined wavelength.

According to embodiments of the present disclosure, determining the concentration of the detected tissue element according to the first output light intensity and the second output light intensity corresponding to each predetermined wavelength may include the following operations.

A differential processing is performed on the first output light intensity and the second output light intensity corresponding to the predetermined wavelength to obtain a differential signal. The concentration of the detected tissue element is determined according to the differential signal corresponding to each predetermined wavelength.

According to embodiments of the present disclosure, since the change in the uncontrollable detection condition is unpredictable and uncontrollable, it is difficult to reduce the influence of the change in the uncontrollable detection condition on the detection result by achieving a reproducibility using an effective control method. In order to improve the detection accuracy, the inventors found that the influence of the uncontrollable detection condition on the detection result may be reduced by using a proper mathematical algorithm, so that the influence on the detection result may be reduced to a negligible level, that is, so that the influence of the change in the uncontrollable detection condition on the detection result is at a similar level to an influence of a random noise on the detection result.

In order to reduce the influence of the change in the uncontrollable detection condition on the detection result, it is possible to adopt an interference suppression method, which may include a differential detection method. The differential detection method may include a temporal differential detection method and a position differential detection method. The differential detection method may be implemented to reduce the influence of the change in the uncontrollable detection condition on the detection result for the following reasons. If the output light intensities corresponding to different average optical paths carry substantially the same interference information, that is, the interference has substantially the same influence on the output light intensities corresponding to different average optical paths, then a differential processing may be performed on the output light intensities corresponding to two average optical paths (that is, the first output light intensity and the second output light intensity) to obtain a differential signal as the output light intensities corresponding to different average optical paths carry different valid information. The concentration of the detected tissue element may be determined according to the differential signal. The interference information may be understood as a response of the output light intensity to the interference. The valid information may be understood as a response of the output light intensity to the detected tissue element.

According to embodiments of the present disclosure, the differential processing performed on the first output light intensity and the second output light intensity corresponding to the predetermined wavelength may include a processing method in terms of hardware and a processing method in terms of software. The processing method in terms of hardware may include processing by using a differential circuit. The processing method in terms of software may include performing a differential operation by using a differential algorithm. The differential algorithm may include a direct differential operation and a logarithmic differential operation. The direct differential operation refers to directly performing a differential processing on two parameters. The logarithmic differential operation refers to performing a logarithmic operation on two parameters to obtain logarithmic parameters, and then performing a differential processing on the two logarithmic parameters.

According to embodiments of the present disclosure, it is possible to effectively weaken a common mode interference information through the differential detection method, thereby improving the detection accuracy.

According to embodiments of the present disclosure, performing the differential processing on the first output light intensity and the second output light intensity corresponding to the predetermined wavelength to obtain the differential signal may include the following operations.

The first output light intensity and the second output light intensity corresponding to the predetermined wavelength are processed using a differential circuit, so as to obtain the differential signal.

According to embodiments of the present disclosure, the differential processing on the first output light intensity and the second output light intensity may be performed using a differential circuit, so as to directly obtain the differential signal.

According to embodiments of the present disclosure, performing the differential processing on the first output light intensity and the second output light intensity corresponding to the predetermined wavelength to obtain the differential signal may include the following operations.

The first output light intensity and the second output light intensity corresponding to the predetermined wavelength are processed using a differential algorithm, so as to obtain the differential signal.

According to embodiments of the present disclosure, processing the first output light intensity and the second output light intensity corresponding to the predetermined wavelength using a differential algorithm to obtain the differential signal may include the following operations.

A direct differential operation is performed on the first output light intensity and the second output light intensity corresponding to the predetermined wavelength, so as to obtain the differential signal.

According to embodiments of the present disclosure, processing the first output light intensity and the second output light intensity corresponding to the predetermined wavelength using a differential algorithm to obtain the differential signal may include the following operations.

A logarithmic processing is performed on the first output light intensity and the second output light intensity corresponding to the predetermined wavelength, so as to obtain a first logarithmic light intensity and a second logarithmic light intensity. A direct differential operation is performed on the first logarithmic light intensity and the second logarithmic light intensity corresponding to the predetermined wavelength, so as to obtain the differential signal.

According to embodiments of the present disclosure, the first logarithmic light intensity represents a logarithm of the first output light intensity, and the second logarithmic light intensity represents a logarithm of the second output light intensity.

The differential signal may be determined by Equation (1).

$$A_D = \ln\left(I(\overline{L_1})\right) - \ln\left(I(\overline{L_2})\right) \quad (1)$$

where $A_D$ represents the differential signal, $I(\overline{L_1})$ represents the first output light intensity, $I(\overline{L_2})$ represents the second output light intensity, $\overline{L_1}$ represents the average optical path corresponding to the first output light intensity, and $\overline{L_2}$ represents the average optical path corresponding to the second output light intensity.

According to embodiments of the present disclosure, the first output light intensity and the second output light intensity are acquired at different time instants by the same or different homogeneous photosensitive surfaces. The first output light intensity is a light intensity in a systole, and the second output light intensity is a light intensity in a diastole. The homogeneous photosensitive surface includes one or more photosensitive surfaces, and the homogeneous photosensitive surface is used to output one output light intensity.

According to embodiments of the present disclosure, in a case that the first output light intensity and the second output light intensity are acquired at different time instants by the same or different homogeneous photosensitive surfaces, the tissue element detection may be performed using a pulse wave-based temporal differential detection method.

A pulse beat, also known as an arterial pulsation, refers to that with a periodic contraction and relaxation of a heart that occurs with heartbeats, a pressure inside an aorta causes a pulsatile change in a diameter of a blood vessel, and a blood flow in the blood vessel also changes regularly and periodically. Each pulse waveform includes an ascending branch and a descending branch. The ascending branch represents a dilation of the artery during a ventricular systole, and the descending branch represents a retraction of the artery during a ventricular diastole. A diastole and a systole of the ventricle represent a pulsation cycle.

According to embodiments of the present disclosure, as the pulse wave-based temporal differential detection method is adopted, it is required to utilize an information of the pulse beat as much as possible. In order to improve the detection accuracy, the photosensitive surface may be arranged at a position as close as possible to the target site (such as a target blood vessel). That is, the homogeneous photosensitive surface for outputting the first output light intensity and the second output light intensity may be arranged at a position from which a distance to the target site is less than or equal to a fourth distance threshold. The fourth distance threshold may be zero, that is, the homogeneous photosensitive surface may be arranged on the target site. The homogeneous photosensitive surface for outputting the first output light intensity and the second output light intensity being arranged at the position from which the distance to the target site is less than or equal to the fourth distance threshold means that the distance from the target site to each photosensitive surface in the homogeneous photosensitive surface for outputting the first output light intensity and the second output light intensity is less than or equal to the fourth distance threshold. The distance from the target site to each photosensitive surface in the homogeneous photosensitive surface being less than or equal to the fourth distance threshold may mean that a distance from the target blood vessel to an edge of the photosensitive surface farthest away from the target site in the homogeneous photosensitive surface is less than or equal to the fourth distance threshold.

It should be noted that utilizing the information of the pulse beat as much as possible when adopting the pulse wave-based temporal differential detection method is not contradictory to the above-mentioned reducing the adverse influences of the pulse beat on the detection result by using the large-area photosensitive surface. The former is to utilize a useful information brought by the pulse beat as much as possible, while the latter is to minimize the adverse influence brought by the pulse beat. In addition, the first output light intensity may also be the light intensity in the diastole, and the second output light intensity may also be the light intensity in the systole. The first output light intensity and the second output light intensity corresponding to the predetermined wavelength may be output light intensities in a same pulsation cycle, or may be output light intensities in different pulsation cycles.

According to embodiments of the present disclosure, the first output light intensity corresponding to the predetermined wavelength is acquired by a first homogeneous photosensitive surface corresponding to the predetermined wavelength, and the second output light intensity corresponding to the predetermined wavelength is acquired by a second homogeneous photosensitive surface corresponding to the predetermined wavelength. The first homogeneous photosensitive surface includes one or more photosensitive surfaces, and the second homogeneous photosensitive surface includes one or more photosensitive surfaces.

For the predetermined wavelength, embodiments of the present disclosure provide the first homogeneous photosensitive surface corresponding to the predetermined wavelength and the second homogeneous photosensitive surface corresponding to the predetermined wavelength. The first homogeneous photosensitive surface is used to output the first output light intensity corresponding to the predetermined wavelength, and the second homogeneous photosensitive surface is used to output the second output light intensity corresponding to the predetermined wavelength. Both the first homogeneous photosensitive surface and the second homogeneous photosensitive surface may include one or more photosensitive surfaces.

According to embodiments of the present disclosure, the first output light intensity and the second output light intensity may be processed using a position differential detection method, so as to determine the concentration of the detected tissue element.

According to embodiments of the present disclosure, it is needed to avoid the target site (such as the target blood vessel) as much as possible when the position differential detection method is adopted. In order to improve the detection accuracy, the photosensitive surface may be arranged as far away from the target site as possible. That is, the first homogeneous photosensitive surface for outputting the first output light intensity may be arranged at a position from which a distance to the target site is greater than or equal to a fifth distance threshold, that is, the distance between each photosensitive surface in the first homogeneous photosensitive surface and the target site is greater than or equal to the fifth distance threshold. The distance between each photosensitive surface in the first homogeneous photosensitive surface and the target site being greater than or equal to the fifth distance threshold may mean that the distance between an edge of the photosensitive surface closest to the target site in the first homogeneous photosensitive surface and the target site is greater than or equal to the fifth distance threshold. Alternatively, the first homogeneous photosensitive surface is in non-contact with the target site, and a distance between a center of the photosensitive surface closest to the target site in the first homogeneous photosensitive surface and the target site is greater than or equal to the fifth distance threshold. The second homogeneous photosensitive surface for outputting the second output light intensity is arranged at a position from which a distance to the target site is greater than or equal to a sixth distance threshold. For the understanding of the second homogeneous photosensitive surface for outputting the second output light intensity being arranged at a position from which the distance to the target site is greater than or equal to the sixth distance threshold, reference may be made to the description of the first homogeneous photosensitive surface for outputting the first output light intensity, and details will not be repeated here.

According to embodiments of the present disclosure, the first homogeneous photosensitive surface and the second homogeneous photosensitive surface are the same homogeneous photosensitive surface, and the exit light received by the first homogeneous photosensitive surface and the exit light received by the second homogeneous photosensitive surface are obtained through a transmission of the incident light incident at different incident positions.

According to embodiments of the present disclosure, the first homogeneous photosensitive surface and the second homogeneous photosensitive surface are different homogeneous photosensitive surfaces.

According to embodiments of the present disclosure, there may be at least two incident positions of the incident light, and the first homogeneous photosensitive surface and the second homogeneous photosensitive surface may be the same photosensitive surface. If the homogeneous photosensitive surface is used to receive the exit light corresponding to the first output light intensity, that is, it is used as the first homogeneous photosensitive surface, then the incident position corresponding to the exit light is a first incident position. If the homogeneous photosensitive surface is used to receive the exit light corresponding to the second output light intensity, that is, it is used as the second homogeneous photosensitive surface, then the incident position corresponding to the exit light is a second incident position. The first incident position and the second incident position are different incident positions.

According to embodiments of the present disclosure, the first homogeneous photosensitive surface and the second homogeneous photosensitive surface may also be different homogeneous photosensitive surfaces.

According to embodiments of the present disclosure, an average optical path of the exit light received at different photosensitive positions of each photosensitive surface in the first homogeneous photosensitive surface is within a first average optical path range. The first average optical path range is determined according to a first optical path mean value, and the first optical path mean value is a mean value calculated according to the average optical paths of the exit light received at the photosensitive positions of the first homogeneous photosensitive surface. An average optical path of the exit light received at different photosensitive positions of each photosensitive surface in the second homogeneous photosensitive surface is within a second average optical path range. The second average optical path range is determined according to a second optical path mean value, and the second optical path mean value is a mean value calculated according to the average optical paths of the exit light received at the photosensitive positions of the second homogeneous photosensitive surface.

According to embodiments of the present disclosure, in order to improve the detection accuracy obtained by performing a tissue element detection using the position differential detection method, it is needed to ensure that the exit light received by the first homogeneous photosensitive surface has a characteristic of a short optical path, and the second homogeneous photosensitive surface also has a characteristic of a short optical path. The short optical path may be understood as that the average optical path of the exit light is within an average optical path range.

For the first homogeneous photosensitive surface, the average optical path of the exit light received at different photosensitive positions of each photosensitive surface in the first homogeneous photosensitive surface is within the first average optical path range. The first average optical path range is determined as follows. A first optical path mean value for the average optical paths of the exit light received at the photosensitive positions of the first homogeneous photosensitive surface is determined, and a first optical path change amplitude is determined. The first average optical path range is determined according to the first optical path mean value and the first optical path change amplitude. For example, if the first optical path mean value is b, and the first optical path change amplitude is ±40%, then the first average optical path range may be greater than or equal to 0.6b and less than or equal to 1.4b.

For the second homogeneous photosensitive surface, the average optical path of the exit light received at different photosensitive positions of each photosensitive surface in the second homogeneous photosensitive surface is within the second average optical path range. The second average optical path range is determined as follows. A second optical path mean value for the average optical paths of the exit light received at the photosensitive positions of the second homogeneous photosensitive surface is determined, and a second optical path change amplitude is determined. The second average optical path range is determined according to the second optical path mean value and the second optical path change amplitude.

According to embodiments of the present disclosure, an absolute value of a difference between the first optical path mean value and the second optical path mean value is within a first optical path difference range.

According to embodiments of the present disclosure, in order to improve the detection accuracy obtained by performing a tissue element detection based on the differential detection method, it is needed to arrange the first homogeneous photosensitive surface and the second homogeneous photosensitive surface within an appropriate position range. A description will be given below by taking blood glucose as an example of the detected tissue element. In a case that the detected tissue element is blood glucose, the target tissue layer is the dermis, and the output light intensity is required to be the output light intensity that mainly carries the tissue element information in the dermis.

First, if the distance between the position of the photosensitive surface and the center of the incident light is too small, the output light intensity of the exit light may mainly carry the tissue element information in the epidermis. If the distance between the position of the photosensitive surface and the center of the incident light is overly large, the output light intensity of the exit light may mainly carry the tissue element information in the subcutaneous fat layer. As the dermis is located between the epidermis and the subcutaneous fat layer, an arrangement position of the first homogeneous photosensitive surface and the second homogeneous photosensitive surface needs to be selected within an appropriate position range, and the distance between the first homogeneous photosensitive surface and the second homogeneous photosensitive surface may not be overly large.

Second, although the differential detection method may be implemented to effectively weaken the common mode interference, it may also lose part of the valid information, i.e., the blood glucose information, while weakening the common mode interference. If two positions are extremely close, it is possible all valid information may be lost. Therefore, the arrangement position of the first homogeneous photosensitive surface and the second homogeneous photosensitive surface needs to be selected within an appropriate position range, and the distance between the first homogeneous photosensitive surface and the second homogeneous photosensitive surface may not be too small.

In order to arrange the first homogeneous photosensitive surface and the second homogeneous photosensitive surface within an appropriate position range, a determination may be made according to a principle of valid information detection, a principle of optimization of differential detection precision, and a principle of effective elimination of interference signals. The principle of valid information detection may mean that the exit light at two positions may carry as much tissue element information as possible in the target tissue layer. Therefore, the two positions should be within a rational position range. The principle of optimization of differential detection precision may mean that there should be a certain distance between two positions, so as to ensure that as much valid information as possible is retained after the differential operation. The principle of effective elimination of interference signals may mean that the distance between two positions should be as small as possible to improve the effect of the differential detection method in eliminating the common mode interference.

Reflected in the optical path, arranging the first homogeneous photosensitive surface and the second homogeneous photosensitive surface within a rational position range requires that the absolute value of the difference between the first optical path mean value corresponding to the first homogeneous photosensitive surface and the second optical path mean value corresponding to the second homogeneous photosensitive surface is within the first optical path difference range. The first optical path difference range is determined according to an optimal differential optical path. The optimal differential optical path may be determined according to at least one of the above three principles.

It may be understood that the requirement for the position arrangement of the first homogeneous photosensitive surface and the second homogeneous photosensitive surface also require that the area of the photosensitive surface may not be overly large, otherwise a differential effect may be affected, thereby affecting the detection accuracy.

According to embodiments of the present disclosure, the first average optical path range is less than or equal to the first optical path difference range, and the second average optical path range is less than or equal to the first optical path difference range.

According to embodiments of the present disclosure, reflected in the optical path, arranging the first homogeneous photosensitive surface and the second homogeneous photosensitive surface within a rational position range further requires that the first average optical path range is less than or equal to the first optical path difference range, and the second average optical path range is less than or equal to the first optical path difference range. It may be concluded that an absolute value of a difference between the first optical path mean value corresponding to the first homogeneous photosensitive surface and the second optical path mean value corresponding to the second homogeneous photosensitive surface is within the first optical path difference range, the first average optical path range is less than or equal to the first optical path difference range, and the second average optical path range is less than or equal to the first optical path difference range.

According to embodiments of the present disclosure, the first optical path difference range is determined according to the optimal differential optical path corresponding to the predetermined wavelength.

According to embodiments of the present disclosure, when the detection region of the detected living object is determined, there exists an optimal differential sensitivity corresponding to the predetermined wavelength. The optimal differential sensitivity may represent a sensitivity in a case of a maximum change in the differential signal caused by the change in the concentration of a unit detected tissue element. The optimal differential optical path may be determined according to the optimal differential sensitivity, that is, the optimal differential optical path may be determined according to the principle of optimization of differential detection precision. Therefore, the optical path corresponding to the optimal differential sensitivity may be referred to as the optimal differential optical path.

According to embodiments of the present disclosure, after the optimal differential optical path corresponding to the predetermined wavelength is determined, an up and down adjustment amplitude may be provided, and the first optical path difference range corresponding to the predetermined wavelength is determined according to the optimal differential optical path corresponding to the predetermined wavelength and the up and down adjustment amplitude.

According to embodiments of the present disclosure, a source-detection distance of each photosensitive surface in the first homogeneous photosensitive surface corresponding to the predetermined wavelength from the center of the incident light is within a predetermined source-detection distance range corresponding to the predetermined wavelength. The predetermined source-detection distance range is determined according to a source-detection distance of a floating reference position corresponding to the predetermined wavelength from the center of the incident light.

According to embodiments of the present disclosure, in order to further improve the detection accuracy, the position of the photosensitive surface may be arranged based on a floating reference method. A description is given below for the floating reference method.

For the detected living object, when the incident light enters the tissue, absorption and scattering may occur, the absorption may directly cause an attenuation of light energy, and the scattering may affect a distribution of the exit light by changing a transmitting direction of photons, and the distribution of the exit light is a result of a combined effect of the absorption and the scattering. Based on the floating reference method, for the detected tissue element, there is a position away from the center of the incident light at which the absorption and the scattering have a same influence on the output light intensity of the exit light and opposite directions, and therefore the exit light is insensitive to the change in the concentration of the detected tissue element. Such position with above characteristics may be referred to as a benchmark position (or a reference position). The output light intensity of the exit light at the benchmark position reflects a response to the interference other than the detected tissue element during the detection process. Moreover, for the detected tissue element, there is also a position away from the center of the incident light at which the sensitivity of the output light intensity of the exit light to the change in the concentration of the detected tissue element is greater than or equal to a sensitivity threshold. Such position with above characteristics may be referred to as a detection position. The output light intensity of the exit light at the detection position reflects a response to the detected tissue element during the detection process and a response to the interference other than the detected tissue element. The benchmark position and the detection position may vary depending on the wavelength, the detected living object, and the detection region. Therefore, the benchmark position may be called a floating reference position.

According to embodiments of the present disclosure, since the output light intensity of the exit light exited from the floating reference position mainly carries the response to the interference other than the detected tissue element during the detection process, the output light intensity of the exit light exited from the floating reference position may be introduced into the differential detection to minimize the common mode interference and minimize the loss of valid information. Based on the above, when the detection region of the detected living object is determined, for each predetermined wavelength, the source-detection distance of at least one of the M photosensitive surfaces from the center of the incident light may be within the predetermined source-detection distance range corresponding to the predetermined wavelength. The predetermined source-detection distance range is determined according to the source-detection distance of the floating reference position corresponding to the predetermined wavelength from the center of the incident light. In embodiments of the present disclosure, the source-detection distance of each photosensitive surface in the first homogeneous photosensitive surface from the center of the incident light may be within the predetermined source-detection distance range corresponding to the predetermined wavelength.

Exemplarily, for the detection region B of the detected living object A, the distance between the floating reference position corresponding to the predetermined wavelength λ1 and the center of the incident light is 1.7 mm, then the predetermined source-detection distance range corresponding to the predetermined wavelength λ1 may be 1.5 mm to 1.9 mm.

Based on the above, the homogeneous photosensitive surface corresponding to the reference position and the homogeneous photosensitive surface corresponding to the detection position may be determined. The output light intensity acquired by the homogeneous photosensitive surface corresponding to the reference position is called the first output light intensity, and the output light intensity acquired by the homogeneous photosensitive surface corresponding to the detection region is called the second output light intensity. Alternatively, the output light intensity acquired by the homogeneous photosensitive surface corresponding to the detection region is called the first output light intensity, and the output light intensity acquired by the homogeneous photosensitive surface corresponding to the reference position is called the second output light intensity.

According to embodiments of the present disclosure, determining the concentration of the at least one detected tissue element according to the at least one output light intensity corresponding to the at least one predetermined wavelength may include the following operations.

In a case of determining the concentration of each detected tissue element in the at least one detected tissue element, for each predetermined wavelength in the at least one predetermined wavelength, a third output light intensity is determined from the at least one output light intensity corresponding to the predetermined wavelength. A differential processing is performed on the third output light intensities corresponding to different predetermined wavelengths, so as to obtain at least one differential signal. The concentration of the detected tissue element is determined according to the at least one differential signal.

According to embodiments of the present disclosure, the third output light intensity may be processed by using a wavelength differential detection method, so as to determine the concentration of the detected tissue element. If the following conditions are met, a tissue element detection may be performed by using the wavelength differential detection method, so as to eliminate the common mode interference and retain sufficient valid information, thereby improving the detection accuracy.

A first condition is that for each detected tissue element, influences of a same interference (such as temperature or pressure) on the output light intensities corresponding to two predetermined wavelengths have consistent or substantially consistent patterns.

A second condition is that there is a great difference in the sensitivities of the output light intensities corresponding to two predetermined wavelengths to the change in the concentration of the detected tissue element.

When the predetermined wavelength is determined, the third output light intensity is determined from at least one output light intensity corresponding to the predetermined wavelength, so that the third output light intensity corresponding to each predetermined wavelength may be obtained. For two predetermined wavelengths, a differential processing may be performed on two third output light intensities to obtain a differential signal.

According to embodiments of the present disclosure, performing the differential processing on the two third output light intensities may include the following operations. The two third output light intensities are processed using a differential circuit, so as to obtain the differential signal. Alternatively, a differential operation is performed on the two third output light intensities by using a differential algorithm, so as to obtain the differential signal. Performing the differential operation on the two third output light intensities using the differential algorithm to obtain the differential signal may include the following operations. A direct differential operation is performed on the two third output light intensities to obtain the differential signal. Alternatively, a logarithmic processing is performed on the two third output light intensities respectively to obtain two logarithmic light intensities, and a direct differential operation is performed on the two logarithmic light intensities to obtain the differential signal.

According to embodiments of the present disclosure, determining the concentration of the detected tissue element according to the differential signal corresponding to each predetermined wavelength may include the following operations.

A direct differential operation is performed on the differential signals corresponding to different predetermined wavelengths, so as to obtain at least one wavelength differential signal. The concentration of the detected tissue element is determined according to the at least one wavelength differential signal.

According to embodiments of the present disclosure, the differential signal may be processed by using a wavelength differential detection method, so as to determine the concentration of the detected tissue element. If the following conditions are met, a tissue element detection may be performed by using the wavelength differential detection method, so as to eliminate the common mode interference and retain sufficient valid information, thereby improving the detection accuracy.

A first condition is that for each detected tissue element, influences of a same interference (such as temperature or pressure) on the differential signals corresponding to two predetermined wavelengths have consistent or substantially consistent patterns.

A second condition is that there is a great difference in the sensitivities of the differential signals corresponding to two predetermined wavelengths to the change in the concentration of the detected tissue element.

For two predetermined wavelengths, a direct differential operation may be performed on two differential signals to obtain a wavelength differential signal. The concentration of the detected tissue element may be determined according to at least one wavelength differential signal.

According to embodiments of the present disclosure, determining the concentration of the at least one detected tissue element according to the at least one output light intensity corresponding to the at least one predetermined wavelength may include the following operations.

In a case of determining the concentration of each detected tissue element in the at least one detected tissue element, for each predetermined wavelength in the at least one predetermined wavelength, at least one superimposed light intensity corresponding to the predetermined wavelength is determined, where the superimposed light intensity is obtained by adding a plurality of output light intensities corresponding to the predetermined wavelength. The concentration of the detected tissue element is determined according to the at least one superimposed light intensity corresponding to each predetermined wavelength.

According to embodiments of the present disclosure, when determining the concentration of the detected tissue elements, it is possible to flexibly use the obtained data according to the actual situation, such as a small value of a single output light intensity, or a low signal-to-noise ratio of the output light intensity, so as to improve the detection accuracy.

Based on the above, for each detected tissue element, when the predetermined wavelength is determined, at least one superimposed light intensity corresponding to the predetermined wavelength may be determined, and the concentration of the detected tissue element may be determined according to the at least one superimposed light intensity corresponding to each predetermined wavelength. The superimposed light intensity may be obtained by adding a plurality of output light intensities. The output light intensity is a light intensity of diffused light (that is, the exit light).

According to embodiments of the present disclosure, determining the concentration of the at least one detected tissue element according to the at least one output light intensity corresponding to the at least one predetermined wavelength may include the following operations.

In a case of determining the concentration of each detected tissue element in the at least one detected tissue element, for each predetermined wavelength in the at least one predetermined wavelength, a fourth output light intensity is determined from the at least one output light intensity corresponding to the predetermined wavelength. The concentration of the detected tissue element is determined according to the fourth output light intensity corresponding to each predetermined wavelength.

According to embodiments of the present disclosure, the tissue element detection may be performed using a non-differential detection method, that is, the concentration of the detected tissue element is determined according to the fourth output light intensity corresponding to each predetermined wavelength.

According to embodiments of the present disclosure, the fourth output light intensity corresponding to the predetermined wavelength is acquired by the homogeneous photosensitive surface corresponding to the predetermined wavelength, and a difference between the average optical path of the exit light received at different photosensitive positions of each photosensitive surface in the homogeneous photosensitive surface and the optimal optical path corresponding to the predetermined wavelength is within the second optical path difference range.

According to embodiments of the present disclosure, in order to improve the detection accuracy, when the detection region of the detected living object is determined, for each predetermined wavelength, the average optical path of the exit light received at different photosensitive positions of the homogeneous photosensitive surface for acquiring the third output light intensity may be close to the optimal optical path corresponding to the predetermined wavelength, that is, an absolute value of a difference between the average optical path of the exit light received at different photosensitive positions of the homogeneous photosensitive surface for acquiring the third output light intensity and the optimal optical path corresponding to the predetermined wavelength is less than or equal to the second optical path difference range. The optimal optical path corresponding to the predetermined wavelength may be understood as the optical path corresponding to the maximum sensitivity to the detected tissue element at the predetermined wavelength.

According to embodiments of the present disclosure, each photosensitive surface includes a ring photosensitive surface or a non-ring photosensitive surface, and different photosensitive surfaces have the same or different shapes.

According to embodiments of the present disclosure, each photosensitive surface may be made of a photosensitive material. The ring photosensitive surface may avoid a problem of an orientation positioning, and may also achieve a large area design within a small source-detection distance range. It should be noted that the source-detection distance is generally an important physical quantity in the living tissue element detection, and it is very meaningful to achieve a large area design within a small source-detection distance.

According to embodiments of the present disclosure, in some cases, using a non-ring photosensitive surface has the following beneficial effects.

In a first aspect, due to the influence of the detection region on the detection result, a photosensitive surface arranged in a detection region conducive to the detection may generally obtain a better detection result than a photosensitive surface arranged in a detection region interfering with the detection. Therefore, the photosensitive surface may be arranged at an appropriate position according to the tissue structure feature. The non-ring photosensitive surface may easily avoid the detection region that interferes with the detection, such as a blood vessel or a wound region. Therefore, a good effect may be achieved by using the non-ring photosensitive surface.

In a second aspect, due to the non-uniformity of the tissue, the same incident light may have different transmission paths in the tissue, and then the exit light exited from different exit positions correspond to different average optical paths. Taking blood glucose as an example of the detected tissue element, a main source of a blood glucose signal is generally the dermis. Therefore, it is required that the exit light is obtained after the incident light is mainly transmitted in the dermis. Accordingly, there are some requirements for the average optical path corresponding to the exit light.

Assuming that a ring photosensitive surface with a corresponding size is designed according to the requirements for the average optical path, it may be considered that the exit light received at different photosensitive positions of the ring photosensitive surface correspond to substantially similar average optical paths and mainly passes through the dermis. The average optical path is within an average optical path range C. In this case, if the skin tissue is uniform, the above conclusion is in line with an actual situation. However, the skin tissue is usually not uniform, and there is a significant difference in the average optical paths corresponding to the exit light received at different photosensitive positions of the same ring photosensitive surface. For example, the exit light received at some photosensitive positions of the ring photosensitive surface corresponds to substantially similar average optical paths, which are within the average optical path range C, while the average optical paths corresponding to the exit light received at the other photosensitive positions of the ring photosensitive surface are quite different from the above, and are not within the average optical path range C. The average optical path of the exit light being within the average optical path range C may indicate that the exit light mainly passes through the dermis, and the average optical path of the exit light being not within the average optical path range C may indicate that the exit light does not mainly pass through the dermis. Since the ring photosensitive surface outputs one output light intensity, the output light intensity obtained using the ring photosensitive surface may have a low signal quality in a case of uneven skin tissue, thereby affecting the detection accuracy.

The non-ring photosensitive surface may be arranged according to the actual situation. For the above example, if the average optical path not within the average optical path range C is within an average optical path range D, then two non-ring photosensitive surfaces may be used. One non-ring photosensitive surface is used to receive the light intensity value of the exit light of which the average optical path is within the average optical path range C, and the other non-ring photosensitive surface is used to receive the light intensity value of the exit light of which the average optical path is within the average optical path range D. The output light intensities of the two non-ring photosensitive surfaces are consistent with the actual situation, which is beneficial to ensure the detection accuracy.

In a third aspect, when the tissue element detection is performed using the pulse wave-based temporal differential detection method, it is required to make full use of a pulse signal, that is, to maximize a difference between the light intensity in the systole and the light intensity in the diastole. However, most of the ring photosensitive surface may not be located above the blood vessel, and an effect of acquiring the pulse signal may be affected, so that the difference between the light intensity in the systole and the light intensity in the diastole is reduced. Therefore, the difference between the light intensity in the systole and the light intensity in the diastole obtained by using the ring photosensitive surface is less than the difference between the light intensity in the systole and the light intensity in the diastole obtained by using the non-ring photosensitive surface.

In a fourth aspect, due to a tissue non-uniformity and the influence of the change in the physiological background on the exit light, there may be a difference between the average optical paths of the exit light received at different photosensitive surfaces having a same source-detection distance from the center of the incident light. Therefore, a differential operation may be performed on the output light intensities acquired at different photosensitive surfaces having the same source-detection distance from the center of the incident light for the tissue element detection. The above may be implemented by the non-ring photosensitive surface, that is, for the same source-detection distance, it is possible to separately arrange at least two non-ring photosensitive surfaces with the center of the incident light as a center, so as to output two output light intensities.

In a fifth aspect, the manufacturing process is not difficult and the manufacturing cost is not high.

Figure 5:
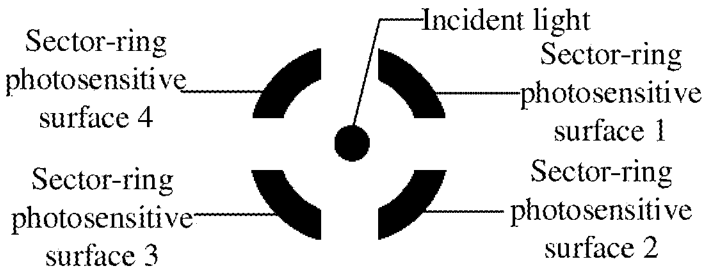
FIG. 5 schematically shows a schematic diagram of a differential detection according to embodiments of the present disclosure.

The fourth aspect will be described below with reference to FIG. 5. FIG. 5 schematically shows a schematic diagram of a differential detection according to embodiments of the present disclosure. As shown in FIG. 5, four sector-ring photosensitive surfaces are shown in FIG. 5, including a sector-ring photosensitive surface 1, a sector-ring photosensitive surface 2, a sector-ring photosensitive surface 3, and a sector-ring photosensitive surface 4. The four sector-ring photosensitive surfaces are separately used, and each sector-ring photosensitive surface has a corresponding output light intensity. Centers of the four sector-ring photosensitive surfaces have a same distance from the center of the incident light, that is, the four sector-ring photosensitive surfaces have the same source-detection distance. Due to the tissue non-uniformity, the average optical path corresponding to the exit light received by the sector-ring photosensitive surface 1 is different from the average optical path corresponding to the exit light received by the sector-ring photosensitive surface 2. A differential operation may be performed according to the output light intensity acquired by the sector-ring photosensitive surface 1 and the output light intensity acquired by the sector-ring photosensitive surface 2, so as to perform a differential detection.

According to embodiments of the present disclosure, the non-ring photosensitive surface includes a sector-ring photosensitive surface, a circular photosensitive surface, a sector photosensitive surface, an elliptical photosensitive surface, or a polygonal photosensitive surface.

According to embodiments of the present disclosure, the polygonal photosensitive surface includes a square photosensitive surface, a rectangular photosensitive surface, or a triangular photosensitive surface.

According to embodiments of the present disclosure, it is possible to design a central angle according to the actual situation, so as to obtain the corresponding sector-ring photosensitive surface, such as a sector-ring photosensitive surface with a central angle of 90°, a sector-ring photosensitive surface with a central angle of 180°, and a sector-ring photosensitive surface with a central angle of 45°.

Figures 6, 7, 8, 9, 10:
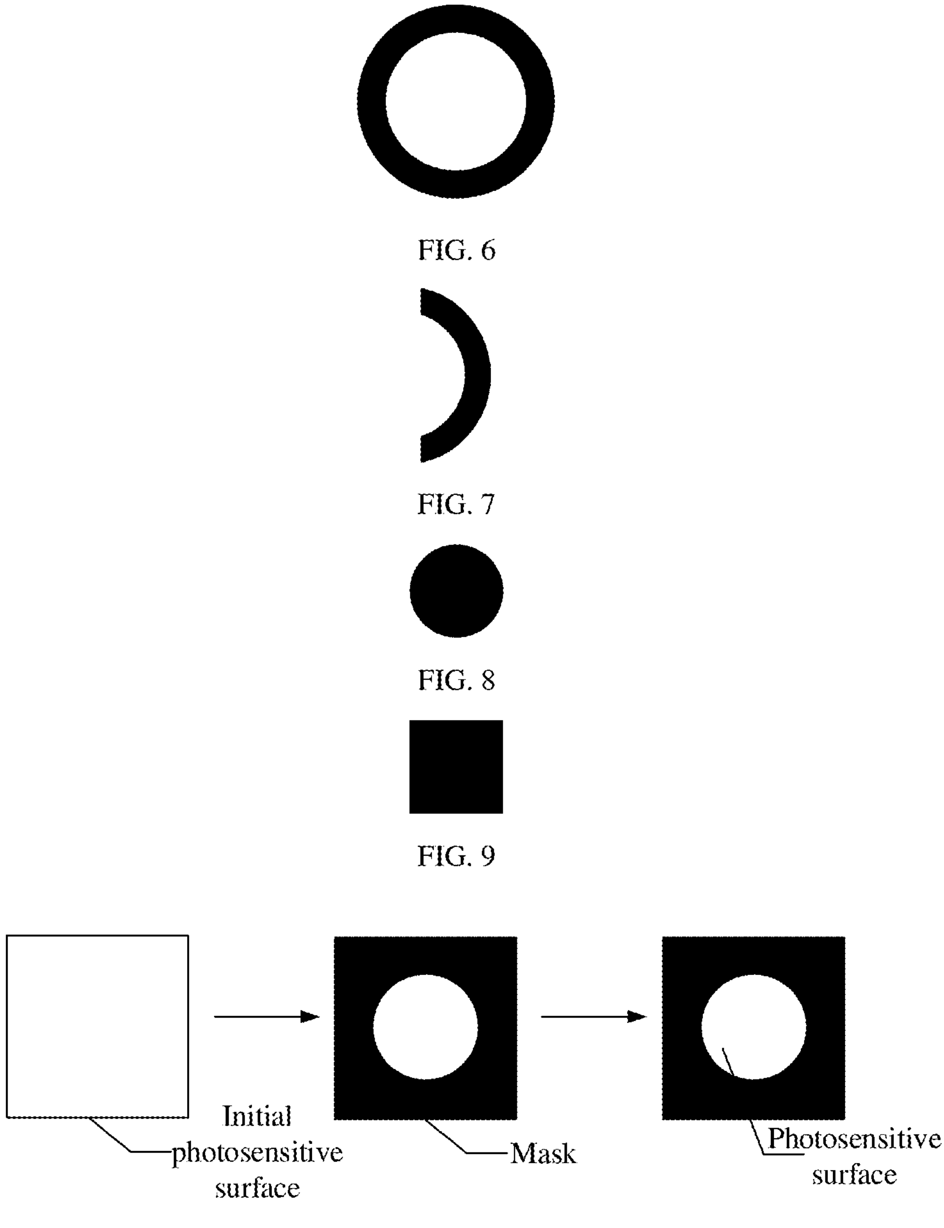
FIG. 6 schematically shows a schematic diagram of a ring photosensitive surface according to embodiments of the present disclosure.
FIG. 7 schematically shows a schematic diagram of a sector-ring photosensitive surface according to embodiments of the present disclosure.
FIG. 8 schematically shows a schematic diagram of a circular photosensitive surface according to embodiments of the present disclosure.
FIG. 9 schematically shows a schematic diagram of a square photosensitive surface according to embodiments of the present disclosure.
FIG. 10 schematically shows a schematic diagram of providing a mask on an initial photosensitive surface to obtain a photosensitive surface according to embodiments of the present disclosure.

According to embodiments of the present disclosure, FIG. 6 schematically shows a schematic diagram of a ring photosensitive surface according to embodiments of the present disclosure. FIG. 7 schematically shows a schematic diagram of a sector-ring photosensitive surface according to embodiments of the present disclosure. FIG. 8 schematically shows a schematic diagram of a circular photosensitive surface according to embodiments of the present disclosure. FIG. 9 schematically shows a schematic diagram of a square photosensitive surface according to embodiments of the present disclosure.

According to embodiments of the present disclosure, the homogeneous photosensitive surface includes a ring photosensitive surface or a non-ring photosensitive surface, the homogeneous photosensitive surface includes one or more photosensitive surfaces, and the homogeneous photosensitive surface is used to output one output light intensity.

According to embodiments of the present disclosure, the homogeneous photosensitive surface may be a ring photosensitive surface or a non-ring photosensitive surface, that is, the homogeneous photosensitive surface overall appears as a ring photosensitive surface or a non-ring photosensitive surface. According to the number of photosensitive surfaces included in the homogeneous photosensitive surface, it may be determined whether an overall shape is formed by a single photosensitive surface or a combination of a plurality of photosensitive surfaces. Each photosensitive surface in the homogeneous photosensitive surface may be a ring photosensitive surface or a non-ring photosensitive surface.

According to embodiments of the present disclosure, the homogeneous photosensitive surface being a ring photosensitive surface may include: the homogeneous photosensitive surface includes one photosensitive surface, and the homogeneous photosensitive surface is an independent ring photosensitive surface; or the homogeneous photosensitive surface includes a plurality of photosensitive surfaces, and the homogeneous photosensitive surface is a ring photosensitive surface formed by combining the plurality of photosensitive surfaces. The homogeneous photosensitive surface being a non-ring photosensitive surface may include: the homogeneous photosensitive surface includes one photosensitive surface, and the homogeneous photosensitive surface is an independent non-ring photosensitive surfaces; or the homogeneous photosensitive surface includes a plurality of photosensitive surfaces, and the homogeneous photosensitive surface is a non-ring photosensitive surface formed by combining the plurality of photosensitive surfaces.

According to embodiments of the present disclosure, the combined plurality of photosensitive surfaces are closely arranged to ensure as much as possible that there is no gap between adjacent photosensitive surfaces. At present, circular photosensitive surfaces or rectangular photosensitive surfaces are commonly used with low difficulty in manufacturing process and low production cost, while photosensitive surfaces of other shapes usually need to be customized with high difficulty in manufacturing process and high production cost. Therefore, in a case of limited production cost, a combination method may be used to combine a plurality of circular photosensitive surfaces and/or a plurality of rectangular photosensitive surfaces to form a homogeneous photosensitive surface with other shapes. The rectangular photosensitive surface may include a square one or an oblong one.

In addition, the production cost of the photosensitive surface is also related to the area of the photosensitive surface. Generally, the larger the area of the photosensitive surface, the higher the production cost. If a large-area photosensitive surface is required and there are currently a plurality of small-area photosensitive surfaces, the plurality of small-area photosensitive surfaces may be combined to obtain a large-area photosensitive surface in order to reduce the production cost.

According to embodiments of the present disclosure, when it is determined that a distance between the homogeneous photosensitive surface and a target site is greater than or equal to a second distance threshold, the homogeneous photosensitive surface includes a ring photosensitive surface, a sector-ring photosensitive surface, a sector photosensitive surface, a circular photosensitive surface, or a square photosensitive surface.

According to embodiments of the present disclosure, when it is determined that the distance between the homogeneous photosensitive surface and the target site is greater than or equal to the second distance threshold, a photosensitive surface with an appropriate shape may be selected according to the jitter of the actual exit light, so as to minimize the adverse influence of the jitter on the detection.

The target site may be a site where the jitter occurs. The pulse beat is one of sources of jitter, and the pulse beat is related to a blood vessel. Therefore, the target site may be a blood vessel. Generally, a jitter distribution of the exit light close to the blood vessel has a particular directionality, while a jitter distribution of the exit light far away from the blood vessel is uniform and has no directionality.

If the homogeneous photosensitive surface is far away from the target site (such as the target blood vessel), the jitter distribution of the exit light may be uniform. In this case, a ring photosensitive surface, a sector-ring photosensitive surface, a sector photosensitive surface, a circular photosensitive surface or a square photosensitive surface may be selected. The homogeneous photosensitive surface being far away from the target site may be understood as that the distance between each photosensitive surface in the homogeneous photosensitive surface and the target site is greater than or equal to the second distance threshold. The distance between each photosensitive surface in the homogeneous photosensitive surface and the target site being greater than or equal to the second distance threshold may include that a distance between an edge of the photosensitive surface closest to the target site in the homogeneous photosensitive surface and the target site is greater than or equal to the second distance threshold value, or the homogeneous photosensitive surface is in non-contact with the target site and the distance between a center of the photosensitive surface closest to the target site in the homogeneous photosensitive surface and the target site is greater than or equal to the second distance threshold value.

In a case that the homogeneous photosensitive surface is far away from the target site, if the average optical path of the exit light received at different photosensitive positions of each photosensitive surface in the homogeneous photosensitive surface is less than or equal to an optical path threshold, it may indicate that the jitter of the exit light is affected by a size of the optical path. The larger the average optical path of the exit light, the more obvious the jitter of the exit light, or otherwise, the less obvious the jitter of the exit light. In this case, it may be designed that the farther away from the center of the incident light, the longer the arc length. Then, it is possible to select a ring photosensitive surface, a sector-ring photosensitive surface, or a sector photosensitive surface.

In a case that the homogeneous photosensitive surface is far away from the target site, if the average optical path of the exit light received at different photosensitive positions of each photosensitive surface in the homogeneous photosensitive surface is greater than the optical path threshold, it may indicate that the jitter of the exit light is almost independent of the size of the optical path. In this case, it is possible to select a circular photosensitive surface or a square photosensitive surface.

According to embodiments of the present disclosure, in a case that the homogeneous photosensitive surface is a sector-ring photosensitive surface, if the homogeneous photosensitive surface includes one photosensitive surface, the sector-ring photosensitive surface is an independent sector-ring photosensitive surface; if the homogeneous photosensitive surface includes a plurality of photosensitive surfaces, the sector-ring photosensitive surface is a photosensitive surface formed by combining the plurality of photosensitive surfaces. Similarly, for the case that the homogeneous photosensitive surface includes a ring photosensitive surface, a circular photosensitive surface, a square photosensitive surface or a sector photosensitive surface, the homogeneous photosensitive surface may be an independently formed homogeneous photosensitive surface or a combined homogeneous photosensitive surface.

It should be noted that at present, circular photosensitive surfaces or rectangular photosensitive surfaces are commonly used with low difficulty in manufacturing process and low production cost, while photosensitive surfaces of other shapes usually need to be customized with high difficulty in manufacturing process and high production cost. Therefore, in a case of limited production cost, the homogeneous photosensitive surface may include a circular photosensitive surface or a rectangle photosensitive surface if the distance between the homogeneous photosensitive surface and the target site is greater than or equal to the second distance threshold.

According to embodiments of the present disclosure, when it is determined that the distance between the homogeneous photosensitive surface and the target site is less than or equal to a third distance threshold, the shape of the homogeneous photosensitive surface is determined according to the jitter distribution of the exit light.

According to embodiments of the present disclosure, if the homogeneous photosensitive surface is close to the target site (such as the target blood vessel), it may indicate that the jitter distribution of the exit light has a particular directionality. In this case, the shape of the homogeneous photosensitive surface may be determined according to the jitter distribution of the exit light. Optionally, the shape of the homogeneous photosensitive surface is a similar figure to the jitter distribution of the exit light. Exemplarily, if the jitter distribution of the exit light is an ellipse, the homogeneous photosensitive surface may be designed as an elliptical photosensitive surface. Alternatively, if the jitter distribution of the exit light is a rectangle, the homogeneous photosensitive surface may be designed as a rectangular photosensitive surface. Alternatively, if the jitter distribution of the exit light is a rhombus, the homogeneous photosensitive surface may be designed as a rhombic photosensitive surface.

According to embodiments of the present disclosure, the jitter distribution of the exit light may be decomposed into a jitter distribution in a first direction and a jitter distribution in a second direction perpendicular to the first direction. A ratio of a length of the homogeneous photosensitive surface in the first direction to a length of the homogeneous photosensitive surface in the second direction is determined according to a ratio of a jitter amplitude of the exit light in the first direction to a jitter amplitude of the exit light in the second direction. The exit light has a maximum jitter amplitude in the first direction.

According to embodiments of the present disclosure, if the jitter distribution of the exit light includes jitter distributions in two mutually perpendicular directions that are obtained by decomposing the jitter distribution of the exit light into the two mutually perpendicular directions which are called the first direction and the second direction respectively, and the exit light has the maximum jitter amplitude in the first direction, then the ratio of the length of the homogeneous photosensitive surface in the first direction to the length of the homogeneous photosensitive surface in the second direction may be determined according to the ratio of the jitter amplitude of the exit light in the first direction to the jitter amplitude of the exit light in the second direction, so that the ratio of the length of the homogeneous photosensitive surface in the first direction to the length of the homogeneous photosensitive surface in the second direction is greater than or equal to the ratio of the jitter amplitude of the exit light in the first direction to the jitter amplitude of the exit light in the second direction.

Exemplarily, if the first direction and the second direction are a Y-axis direction and an X-axis direction in a rectangular coordinate system respectively, then a ratio of the jitter amplitude of the exit light in the Y-axis direction to the jitter amplitude of the exit light in the X-axis direction may be represented by $$\frac{V_y}{V_x},$$

and a ratio of the length of the homogeneous photosensitive surface in the Y-axis direction to the length of the homogeneous photosensitive surface in the X-axis direction may be represented by $$\frac{dy}{dx}, \frac{dy}{dx} \geq \frac{V_y}{V_x}.$$

According to embodiments of the present disclosure, the homogeneous photosensitive surface includes a rectangular photosensitive surface or an elliptical photosensitive surface. A ratio of a length to a width of the rectangular photosensitive surface is determined according to the ratio of the jitter amplitude of the exit light in the first direction to the jitter amplitude of the exit light in the second direction. A ratio of a major axis to a minor axis of the elliptical photosensitive surface is determined according to the ratio of the jitter amplitude of the exit light in the first direction to the jitter amplitude of the exit light in the second direction.

According to embodiments of the present disclosure, if the distance between the homogeneous photosensitive surface and the target site is less than or equal to the third distance threshold, and the jitter distribution of the exit light includes a jitter distribution in the first direction and a jitter distribution in the second direction perpendicular to the first direction, then the homogeneous photosensitive surface may include a rectangular photosensitive surface or an elliptical photosensitive surface. A ratio of a length to a width of the rectangular photosensitive surface is greater than or equal to the ratio of the jitter amplitude of the exit light in the first direction to the jitter amplitude of the exit light in the second direction. A ratio of a major axis to a minor axis of the elliptical photosensitive surface is greater than or equal to the ratio of the jitter amplitude of the exit light in the first direction to the jitter amplitude of the exit light in the second direction.

According to embodiments of the present disclosure, each output light intensity being obtained by processing the light intensity value of the exit light acquired by one or more photosensitive surfaces may include the following operations.

One or more photosensitive surfaces are used in combination to output an output light intensity. Alternatively, each of the one or more photosensitive surfaces is used separately, and the light intensity value of the exit light acquired by each photosensitive surface is calculated to obtain an output light intensity.

According to embodiments of the present disclosure, a photosensitive surface for outputting an output light intensity is referred to as a homogeneous photosensitive surface, and the homogeneous photosensitive surface may include one or more photosensitive surfaces. A condition for using different photosensitive surfaces in combination may be that for each photosensitive surface, the average optical path of the exit light received by the photosensitive surface is within the average optical path range. The average optical path range may be a range greater than or equal to a first average optical path threshold and less than or equal to a second average optical path threshold. The first average optical path threshold and the second average optical path threshold may be determined according to the optical path mean value and the optical path change amplitude. The optical path mean value is a mean value calculated according to the average optical paths of the exit light received at the photosensitive positions of the homogeneous photosensitive surface.

The photosensitive surface is generally used in cooperation with an amplification circuit corresponding to the photosensitive surface, so as to output a light intensity value. In order to allow the homogeneous photosensitive surface to output an accurate output light intensity, it is required that a product of a light response rate of each photosensitive surface in the homogeneous photosensitive surface and an amplification factor of the amplification circuit used in cooperation with the photosensitive surface is a predetermined value. When the product of the light response rate of each photosensitive surface and the amplification factor of the amplification circuit used in cooperation with the photosensitive surface is a same predetermined value, the homogeneous photosensitive surface may output one output light intensity. If the product of the light response rate of a photosensitive surface and the amplification factor of the amplification circuit used in cooperation with the photosensitive surface is a different predetermined value, it is needed to adopt a corresponding method so that the product is the same predetermined value.

The homogeneous photosensitive surface outputting one output light intensity may be achieved by a hardware method or a software method.

In a first method, which is the hardware method, cathodes of different photosensitive surfaces in the homogeneous photosensitive surface may be electrically connected to each other, and anodes of different photosensitive surfaces in the homogeneous photosensitive surface may be electrically connected to each other, that is, a common-cathode common-anode electrical connection between different photosensitive surfaces may be achieved. In this case, it is equivalent to connecting different photosensitive surfaces in parallel so that one or more photosensitive surfaces are used in combination to output one output light intensity. It should be noted that the light response rates of different photosensitive surfaces need to be as consistent as possible to obtain an accurate output light intensity.

In a second method, which is the software method, the cathodes of different photosensitive surfaces in the homogeneous photosensitive surface are not connected to each other, and the anodes of different photosensitive surfaces in the homogeneous photosensitive surface are not connected to each other, that is, each photosensitive surface is used separately to output a light intensity value. After the light intensity value corresponding to each photosensitive surface is obtained, a weight summation may be performed on the light intensity values of the photosensitive surfaces in the homogeneous photosensitive surface by using a corresponding algorithm, so as to obtain one output light intensity.

Alternatively, the output light intensity corresponding to the homogeneous photosensitive surface may be determined by Equation (2) and Equation (3).

$$I = \sum_{i=1}^{N} \alpha_i I_i \tag{2}$$

$$\alpha_i = \frac{H}{\beta_i \gamma_i} \tag{3}$$

where I represents the output light intensity corresponding to the homogeneous photosensitive surface, $I_i$ represents the light intensity value corresponding to the photosensitive surface i, $i \in \{1, 2, \ldots, N-1, N\}$, N represents the number of photosensitive surfaces included in the homogeneous photosensitive surface, $1 \leq N \leq M$, M represents a total number of photosensitive surfaces, $\alpha_1$ represents a weighting coefficient corresponding to the photosensitive surface i, H represents the predetermined value, $\beta_i$ represents the light response rate corresponding to the photosensitive surface i, $\gamma_i$ represents the amplification factor of the amplification circuit used in cooperation with the photosensitive surface i.

According to embodiments of the present disclosure, the output light intensity is a light intensity value of converged exit light acquired by the photosensitive surface.

According to embodiments of the present disclosure, in order to receive a large area exit region using a small area photosensitive surface, a converging method may be used, that is, the exit light exited from each exit position may be converged using a converging method, so that the photosensitive surface may acquire the light intensity value of the converged exit light. The converging method may be implemented by using a photosensitive surface in cooperation with a lens. It should be noted that the small area of the photosensitive surface is relative to the exit region, and the exit region has a large area.

According to embodiments of the present disclosure, the photosensitive surface may be designed to have a small area, so that the cost may be reduced, while the efficiency of the photosensitive surface receiving the exit light may not be greatly affected.

According to embodiments of the present disclosure, each photosensitive surface is used to acquire the light intensity value of the exit light corresponding to a target wavelength. The target wavelength belongs to the plurality of predetermined wavelengths.

According to embodiments of the present disclosure, generally, in order to achieve the detection of light having a plurality of wavelengths, it is possible to adopt a time-division detection method, that is, to perform a detection of light having one predetermined wavelength at one time. In order to achieve a simultaneous detection of light having a plurality of predetermined wavelengths, for each predetermined wavelength, the photosensitive surface may be designed to acquire the light intensity value of the exit light corresponding to the target wavelength. The target wavelength refers to a predetermined wavelength corresponding to the light intensity value of the exit light that may be acquired by the photosensitive surface. Alternatively, a method of providing a corresponding filter film on the photosensitive surface may be adopted.

According to embodiments of the present disclosure, the photosensitive surface is obtained by providing a mask on an initial photosensitive surface, and a light transmittance of the mask is less than or equal to a light transmittance threshold.

According to embodiments of the present disclosure, a shape of the mask is determined according to the shape of the jitter distribution of the exit light.

According to embodiments of the present disclosure, at present, circular photosensitive surfaces or rectangular photosensitive surfaces are commonly used with a low difficulty in manufacturing process and a low production cost, while photosensitive surfaces of other shapes usually need to be customized with a high difficulty in manufacturing process and a high production cost. Therefore, in a case of limited production cost, it is possible to adopt a method of providing a mask on the initial photosensitive surface. A part of the initial photosensitive surface that is blocked by the mask is difficult to receive a light intensity value because the light transmittance of the mask is less than or equal to the light transmittance threshold.

Based on the above, the shape and the position of the mask may be determined according to actually required shape and area, so as to obtain a photosensitive surface with a predetermined shape and area. The actually required shape and area may be determined according to the jitter distribution of the exit light.

Exemplarily, FIG. 10 schematically shows a schematic diagram of providing a mask on an initial photosensitive surface to obtain a photosensitive surface according to embodiments of the present disclosure. In FIG. 10, the initial photosensitive surface is a square photosensitive surface, and the photosensitive surface is a circular photosensitive surface.

According to embodiments of the present disclosure, the light spot irradiated with the incident light on the detection region has a uniform intensity distribution.

According to embodiments of the present disclosure, in order to relax the requirement for the detected living object when performing the tissue element detection so as to ensure the detection accuracy better, it is possible to adopt a method of ensuring a uniform intensity distribution of the light spot irradiated with the incident light on the detection region. Furthermore, the more uniform the intensity distribution of the light spot irradiated with the incident light on the detection region, the lower the requirement for the reproducibility of the controllable detection condition, and the better the effect of reducing the influence of the uncontrollable detection condition on the detection result by using the differential detection method, thereby ensuring the detection accuracy better. Moreover, when a measure to obtain a uniform intensity distribution of the light spot irradiated with the incident light on the detection region is adopted, a light energy of the incident light may be attenuated to a certain extent. However, the tissue element detection requires that the light energy of the incident light may not be too small Therefore, it is needed to ensure a minimum attenuation of the light energy of the incident light while ensuring the uniform intensity distribution of the light spot irradiated with the incident light on the detection region. In addition, if the incident light is transmitted by an optical fiber, the uniform intensity distribution of the light spot of the incident light on the detection region may also reduce an adverse influence of an optical fiber jitter on the detection result.

According to embodiments of the present disclosure, an area of the light spot irradiated with the incident light on the detection region is larger than or equal to a light spot area threshold.

According to embodiments of the present disclosure, in order to relax the requirement for the detected living object when performing the tissue element detection so as to ensure the detection accuracy better, it is possible to make the area of the light spot irradiated with the incident light on the detection region larger than or equal to the light spot area threshold. Furthermore, within a certain range, the larger the area of the light spot irradiated with the incident light on the detection region, the lower the requirement for the reproducibility of the controllable detection condition, and the better the effect of reducing the influence of the uncontrollable detection condition on the detection result by using the differential detection method, thereby ensuring the detection accuracy better. The light spot area threshold may be determined according to actual situation, and is not specifically limited here. In addition, if the incident light is transmitted by an optical fiber, the area of the light spot irradiated with the incident light on the detection region that is larger than or equal to the light spot area threshold may reduce the adverse influence of the optical fiber jitter on the detection result.

Figure 11:
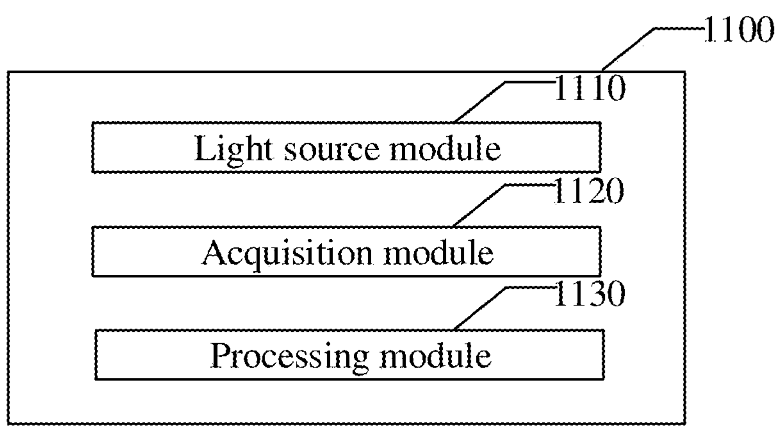
FIG. 11 schematically shows a block diagram of a device of detecting a living tissue element according to embodiments of the present disclosure.

FIG. 11 schematically shows a block diagram of a device of detecting a living tissue element according to embodiments of the present disclosure.

As shown in FIG. 11, a device 1100 of detecting a living tissue element includes a light source module 1110, an acquisition module 1120, and a processing module 1130.

The light source module 1110 is used to irradiate a detection region by incident light having at least one predetermined wavelength. The incident light passes through the detection region to form at least one beam of exit light exited from at least one exit position, and the incident light is incident on at least two incident positions.

The acquisition module 1120 includes M photosensitive surfaces, and each photosensitive surface may acquire a light intensity value of the exit light exited from the exit position within a predetermined anti-jitter range corresponding to the photosensitive surface. The acquisition module 1120 is used to obtain the light intensity value corresponding to each beam of the exit light acquired by the M photosensitive surfaces, so as to obtain T output light intensities. Each output light intensity is obtained by processing the light intensity value of the exit light acquired by one or more photosensitive surfaces.

The processing module 1130 is used to determine a concentration of at least one detected tissue element according to at least one output light intensity corresponding to the at least one predetermined wavelength.

According to the technical solutions of embodiments of the present disclosure, the photosensitive surface may acquire the light intensity value of the exit light exited from the exit position within the corresponding predetermined anti-jitter range. In the photosensitive surface with the above-mentioned characteristics, a ratio of the area that may stably receive the exit light to the area of the photosensitive surface is increased, so that the stability of receiving the exit light is improved, the adverse influence of the change in the intensity distribution of the exit light caused by the jitter is reduced, and the detection accuracy is improved.

According to embodiments of the present disclosure, a ratio of a transmission optical path of the exit light received by each photosensitive surface in the target tissue layer to a total optical path is greater than or equal to a ratio threshold. The total optical path is a total distance that the exit light travels in the detection region.

According to embodiments of the present disclosure, a total area of the homogeneous photosensitive surface is determined according to the tissue structure feature in the detection region. The homogeneous photosensitive surface includes one or more photosensitive surfaces, and the homogeneous photosensitive surface is used to output one output light intensity.

According to embodiments of the present disclosure, a ratio of an area of each photosensitive surface to a circumference of the photosensitive surface is greater than or equal to a ratio threshold.

According to embodiments of the present disclosure, the ratio threshold is greater than or equal to 0.04 mm.

According to embodiments of the present disclosure, the photosensitive surface is in contact or non-contact with the surface of the detection region.

According to embodiments of the present disclosure, a distance between the photosensitive surface and the surface of the detection region is less than or equal to a first distance threshold, and an efficiency of the photosensitive surface receiving the exit light is greater than or equal to an efficiency threshold.

According to embodiments of the present disclosure, an included angle between each part of the photosensitive surface and a direction of the corresponding incident light is greater than or equal to 0° and less than or equal to 360°.

According to embodiments of the present disclosure, the included angle between each part of the photosensitive surface and the direction of the corresponding incident light is greater than or equal to 0° and less than or equal to 360°, so as to achieve a diffusion detection. According to embodiments of the present disclosure, an appropriate position of the photosensitive surface may be determined according to a wavelength feature and/or a detection region feature. The wavelength feature may include a penetration depth of wavelength, and the detection region feature may include a thickness of detection region. Alternatively, the included angle between each part of the photosensitive surface and the direction of the corresponding incident light may generally be a predetermined angle.

Exemplarily, if the wavelength has a large penetration depth and/or the detection region has a small thickness, the position of the photosensitive surface and the incident position of the corresponding incident light may be arranged on different sides of the detection region. If the wavelength has a small penetration depth and/or the detection region has a large thickness, the position of the photosensitive surface and the incident position of the corresponding incident light may be arranged on a same side of the detection region.

Figure 12:
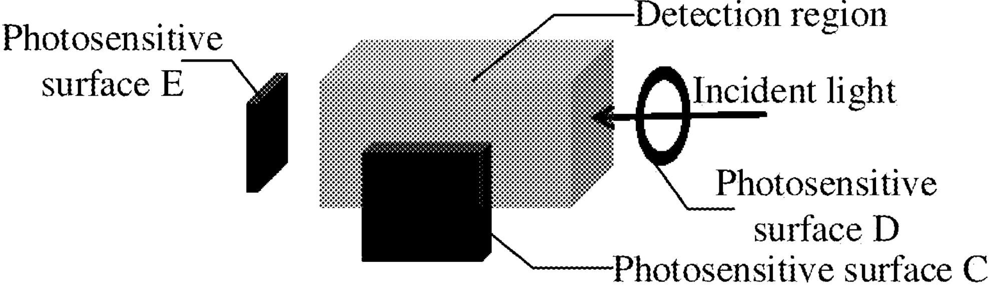
FIG. 12 schematically shows a schematic diagram of a diffusion detection according to embodiments of the present disclosure.

Exemplarily, FIG. 12 schematically shows a schematic diagram of a diffusion detection according to embodiments of the present disclosure. In FIG. 12, the included angle between the photosensitive surface C and the incident light is 90°, the position of the photosensitive surface D and the position of the incident light are arranged on the same side of the detection region, and the position of the photosensitive surface E and the position of the incident light are arranged on different sides of the detection region.

According to embodiments of the present disclosure, the M photosensitive surfaces include one or more homogeneous photosensitive surfaces corresponding to each predetermined wavelength. The homogeneous photosensitive surface is used to acquire the first output light intensity and/or the second output light intensity corresponding to the predetermined wavelength at different time instants. The first output light intensity is a light intensity in a systole, and the second output light intensity is a light intensity in a diastole. The homogeneous photosensitive surface includes one or more photosensitive surfaces. The processing module 1130 is used to determine the concentration of the at least one detected tissue element according to the first output light intensity and the second output light intensity corresponding to each predetermined wavelength.

According to embodiments of the present disclosure, the M photosensitive surfaces include a first homogeneous photosensitive surface and a second homogeneous photosensitive surface corresponding to each predetermined wavelength. The first homogeneous photosensitive surface is used to acquire the first output light intensity corresponding to the predetermined wavelength, and the second homogeneous photosensitive surface is used to acquire the second output light intensity corresponding to the predetermined wavelength. The first homogeneous photosensitive surface includes one or more photosensitive surfaces, and the second homogeneous photosensitive surface includes one or more photosensitive surfaces. The processing module 1130 is used to determine the concentration of the at least one detected tissue element according to the first output light intensity and the second output light intensity corresponding to each predetermined wavelength.

According to embodiments of the present disclosure, the first homogeneous photosensitive surface and the second homogeneous photosensitive surface are the same homogeneous photosensitive surface, and the exit light received by the first homogeneous photosensitive surface and the exit light received by the second homogeneous photosensitive surface are obtained by a transmission of the incident light incident on different incident positions.

According to embodiments of the present disclosure, the first homogeneous photosensitive surface and the second homogeneous photosensitive surface are different homogeneous photosensitive surfaces.

According to embodiments of the present disclosure, the average optical length of the exit light received at different photosensitive positions of each photosensitive surface in the first homogeneous photosensitive surface is within a first average optical path range, the first average optical path range is determined according to the first optical path mean value, and the first optical path mean value is a mean value calculated according to the average optical path of the exit light received at the photosensitive positions of the first homogeneous photosensitive surface. The average optical path of the exit light received at different photosensitive positions of each photosensitive surface in the second homogeneous photosensitive surface is within a second average optical path range, the second average optical path range is determined according to a second optical path mean value, and the second optical path mean value is a mean value calculated according to the average optical path of the exit light received at the photosensitive positions of the second homogeneous photosensitive surface.

According to embodiments of the present disclosure, an absolute value of a difference between the first optical path mean value and the second optical path mean value is within a first optical path difference range.

According to embodiments of the present disclosure, the first average optical path range is less than or equal to the first optical path difference range, and the second average optical path range is less than or equal to the first optical path difference range.

According to embodiments of the present disclosure, the first optical path difference range is determined according to an optimal differential optical path corresponding to the predetermined wavelength.

According to embodiments of the present disclosure, a source-detection distance of each photosensitive surface in the first homogeneous photosensitive surface corresponding to the predetermined wavelength from the center of the incident light is within a predetermined source-detection distance range corresponding to the predetermined wavelength. The predetermined source-detection distance range is determined according to a source-detection distance of a floating reference position corresponding to the predetermined wavelength from the center of the incident light.

According to embodiments of the present disclosure, the M photosensitive surfaces include a homogeneous photosensitive surface corresponding to each predetermined wavelength. The homogeneous photosensitive surface is used to acquire a third output light intensity corresponding to the predetermined wavelength, and the homogeneous photosensitive surface includes one or more photosensitive surfaces. The processing module 1130 is used to perform a differential processing on the third output light intensities corresponding to different predetermined wavelengths to obtain at least one differential signal, and determine the concentration of the detected tissue element according to the at least one differential signal.

According to embodiments of the present disclosure, the processing module 1130 is used to perform a differential processing on the first output light intensity and the second output light intensity corresponding to the predetermined wavelength to obtain a differential signal, perform a direct differential operation on the differential signals corresponding to different predetermined wavelengths to obtain at least one wavelength differential signal, and determine the concentration of the detected tissue element according to the at least one wavelength differential signal.

According to embodiments of the present disclosure, the M photosensitive surfaces include a homogeneous photosensitive surface corresponding to each predetermined wavelength. The homogeneous photosensitive surface is used to acquire a fourth output light intensity corresponding to the predetermined wavelength, and the homogeneous photosensitive surface includes one or more photosensitive surfaces. The processing module 1130 is used to determine the concentration of the at least one detected tissue element according to the fourth output light intensity corresponding to each predetermined wavelength.

According to embodiments of the present disclosure, a difference between the average optical path of the exit light received at different photosensitive positions of each homogeneous photosensitive surface in the homogeneous photosensitive surface and the optimal optical path corresponding to the predetermined wavelength is within a second optical path difference range.

According to embodiments of the present disclosure, each photosensitive surface includes a ring photosensitive surface or a non-ring photosensitive surface, and different photosensitive surfaces have the same or different shapes.

According to embodiments of the present disclosure, the non-ring photosensitive surface includes a sector-ring photosensitive surface, a circular photosensitive surface, a sector photosensitive surface, an elliptical photosensitive surface, or a polygonal photosensitive surface.

According to embodiments of the present disclosure, the polygonal photosensitive surface includes a square photosensitive surface, a rectangular photosensitive surface, or a triangular photosensitive surface.

According to embodiments of the present disclosure, the homogeneous photosensitive surface includes a ring photosensitive surface or a non-ring photosensitive surface. The homogeneous photosensitive surface includes one or more photosensitive surfaces, and the homogeneous photosensitive surface is used to output one output light intensity.

According to embodiments of the present disclosure, the homogeneous photosensitive surface being a ring photosensitive surface includes: the homogeneous photosensitive surface includes one photosensitive surface, and the homogeneous photosensitive surface is an independent ring photosensitive surface; the homogeneous photosensitive surface includes a plurality of photosensitive surfaces, and the homogeneous photosensitive surface is a ring photosensitive surface formed by combining the plurality of photosensitive surfaces. The homogeneous photosensitive surface being a non-ring photosensitive surface includes: the homogeneous photosensitive surface includes one photosensitive surface, and the homogeneous photosensitive surface is an independent non-ring photosensitive surfaces; the homogeneous photosensitive surface includes a plurality of photosensitive surfaces, and the homogeneous photosensitive surface is a non-ring photosensitive surface formed by combining the plurality of photosensitive surfaces.

According to embodiments of the present disclosure, when it is determined that the distance between the homogeneous photosensitive surface and the target site is greater than or equal to the first distance threshold, the homogeneous photosensitive surface includes a ring photosensitive surface, a sector-ring photosensitive surface, a sector photosensitive surface, a circular photosensitive surface, or a square photosensitive surface.

According to embodiments of the present disclosure, when it is determined that the distance between the homogeneous photosensitive surface and the target site is less than or equal to the second distance threshold, the shape of the homogeneous photosensitive surface is determined according to the jitter distribution of the exit light.

According to embodiments of the present disclosure, the jitter distribution of the exit light may be decomposed into a jitter distribution in the first direction and a jitter distribution in the second direction perpendicular to the first direction. A ratio of a length of the homogeneous photosensitive surface in the first direction to a length of the homogeneous photosensitive surface in the second direction is determined according to a ratio of a jitter amplitude of the exit light in the first direction to a jitter amplitude of the exit light in the second direction. The exit light has a maximum jitter amplitude in the first direction.

According to embodiments of the present disclosure, the homogeneous photosensitive surface includes a rectangular photosensitive surface or an elliptical photosensitive surface. A ratio of a length to a width of the rectangular photosensitive surface is determined according to the ratio of the jitter amplitude of the exit light in the first direction to the jitter amplitude of the exit light in the second direction. A ratio of a major axis to a minor axis of the elliptical photosensitive surface is determined according to the ratio of the jitter amplitude of the exit light in the first direction to the jitter amplitude of the exit light in the second direction.

According to embodiments of the present disclosure, the anodes of different photosensitive surfaces among the M photosensitive surfaces are not electrically connected to each other, the anodes of some photosensitive surfaces are electrically connected to each other, or the anodes of all the photosensitive surfaces are electrically connected to each other.

According to embodiments of the present disclosure, each of the M photosensitive surfaces may be used independently. In this case, the anodes of different photosensitive surfaces among the M photosensitive surfaces are not electrically connected to each other.

Some photosensitive surfaces among the M photosensitive surfaces may be used in combination. In this case, the anodes of the different photosensitive surfaces used in combination are electrically connected to each other.

All the photosensitive surfaces of the M photosensitive surfaces may be used in combination. In this case, the anodes of the different photosensitive surfaces used in combination are electrically connected to each other.

Figure 13:
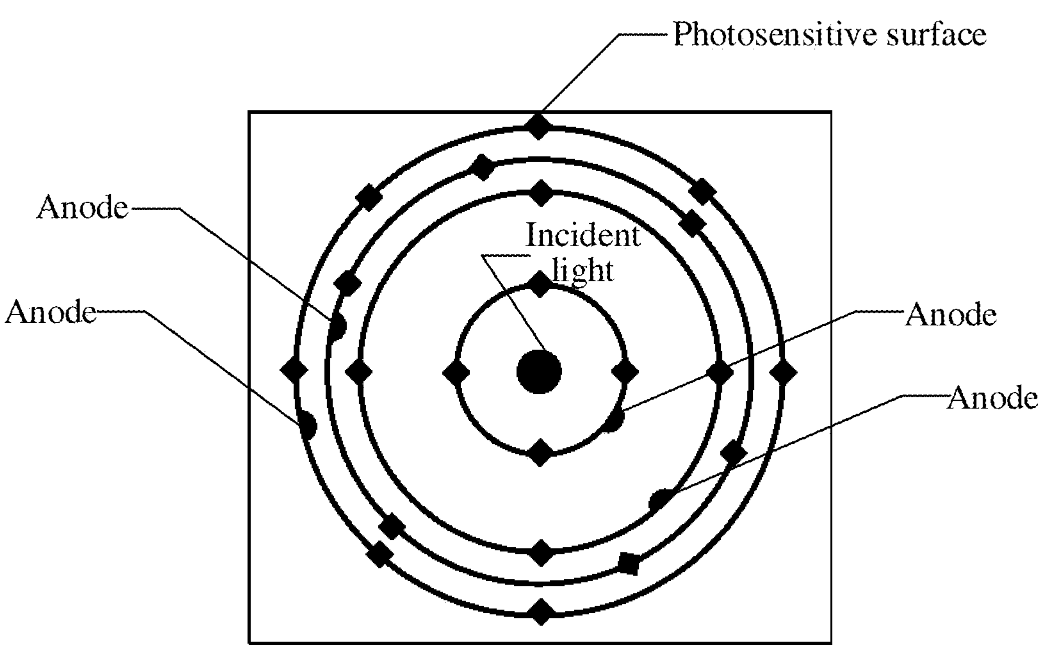
FIG. 13 schematically shows a schematic diagram of an electrical connection of anodes of different photosensitive surfaces according to embodiments of the present disclosure.

According to embodiments of the present disclosure, FIG. 13 schematically shows a schematic diagram of an electrical connection of the anodes of different photosensitive surfaces according to embodiments of the present disclosure. As shown in FIG. 13, the anodes of all the photosensitive surfaces are electrically connected to each other.

According to embodiments of the present disclosure, different parts of a photosensitive surface may be on a same plane or on different planes.

According to embodiments of the present disclosure, the photosensitive surface may be a planar photosensitive surface or a three-dimensional photosensitive surface. If different parts of the photosensitive surface are on the same plane, the photosensitive surface is a planar photosensitive surface. If different parts of the photosensitive surface are on different planes, the photosensitive surface is a three-dimensional photosensitive surface. Whether to use the planar photosensitive surface or the three-dimensional photosensitive surface may be specifically determined according to actual situations, which is not specifically limited here.

Optionally, for a contact detection, in order to improve the detection accuracy, it is needed to ensure a good fitting state between a target surface of the photosensitive surface and a skin surface at the detection region as much as possible. The target surface of the photosensitive surface represents a surface close to the detection region. A flatness of the skin surface at the detection region may not be high. If a planar photosensitive surface is used, it may be difficult to achieve a good fitting state between the target surface of the photosensitive surface and the skin surface at the detection region. The three-dimensional photosensitive surface is a photosensitive surface with different parts on different planes and may be used for the contact detection. A specific form of the three-dimensional photosensitive surface may be determined according to the tissue structure feature of the detection region.

Figure 14:
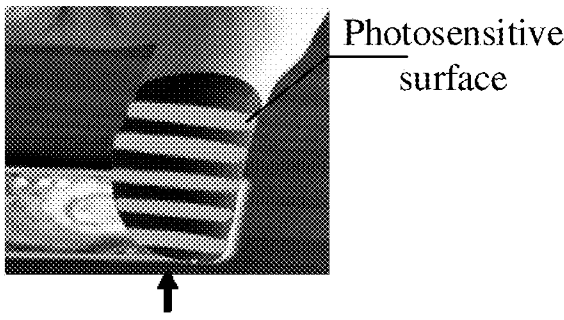
FIG. 14 schematically shows a schematic diagram of a three-dimensional photosensitive surface in a form of a finger cuff according to embodiments of the present disclosure.
Figure 15:
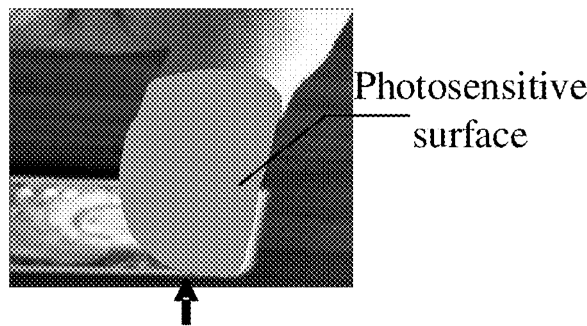
FIG. 15 schematically shows a schematic diagram of another three-dimensional photosensitive surface in a form of a finger cuff according to embodiments of the present disclosure.

FIG. 14 schematically shows a schematic diagram of a three-dimensional photosensitive surface in a form of a finger cuff according to embodiments of the present disclosure. FIG. 15 schematically shows a schematic diagram of another three-dimensional photosensitive surface in a form of a finger cuff according to embodiments of the present disclosure.

Figure 16:
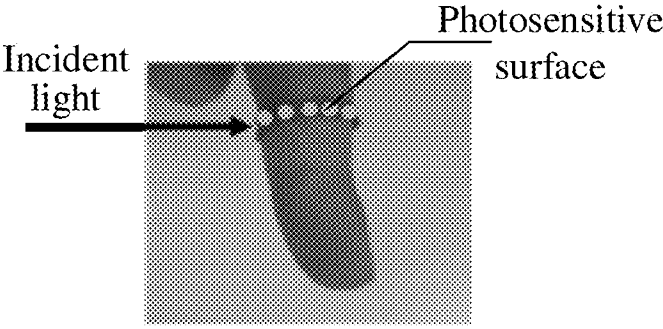
FIG. 16 schematically shows a schematic diagram of a three-dimensional photosensitive surface in a form of a finger ring according to embodiments of the present disclosure.
Figure 17:
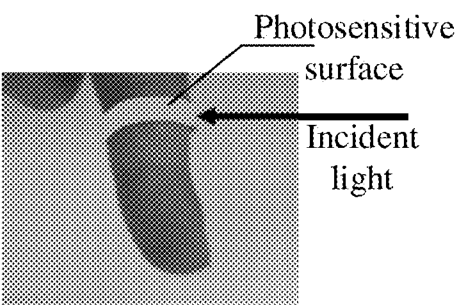
FIG. 17 schematically shows a schematic diagram of another three-dimensional photosensitive surface in a form of a finger ring according to embodiments of the present disclosure.

FIG. 16 schematically shows a schematic diagram of a three-dimensional photosensitive surface in a form of a finger ring according to embodiments of the present disclosure. FIG. 17 schematically shows a schematic diagram of another three-dimensional photosensitive surface in a form of a finger ring according to embodiments of the present disclosure.

Figure 18:
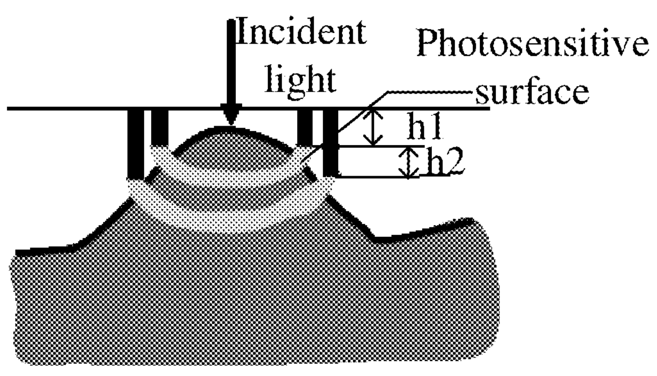
FIG. 18 schematically shows a schematic diagram of a three-dimensional photosensitive surface for an on-arm detection according to embodiments of the present disclosure.

FIG. 18 schematically shows a schematic diagram of a three-dimensional photosensitive surface for an on-arm detection according to embodiments of the present disclosure. In FIG. 18, distances between different parts of the photosensitive surface and a predetermined plane may be determined according to a tissue structure feature of the arm. In FIG. 18, $h_1$ and $h_2$ represent distances between different parts of the photosensitive surface and the predetermined plane.

According to embodiments of the present disclosure, a set of photosensitive surfaces is on a same plane or on different planes, and the set of photosensitive surfaces includes a plurality of photosensitive surfaces.

According to embodiments of the present disclosure, each photosensitive surface included in the set of photosensitive surfaces may be a planar photosensitive surface or a three-dimensional photosensitive surface. If the set of photosensitive surfaces includes a plurality of planar photosensitive surfaces, a photosensitive surface form of three-dimensional photosensitive surface may be presented by the set of photosensitive surfaces by arranging some or all of the plurality of planar photosensitive surfaces on different planes.

It should be noted that a three-dimensional photosensitive surface formed by a plurality of planar photosensitive surfaces may also achieve the above-mentioned effect for the contact detection, and details will not be repeated here.

According to embodiments of the present disclosure, the device 1100 of detecting the living tissue element further includes a converging module arranged between the detection region and the photosensitive surface. The converging module is used to converge the exit light so that the output light intensity is a light intensity value of the converged exit light acquired by the photosensitive surface.

According to embodiments of the present disclosure, in order to receive a large area exit region using a small area photosensitive surface, a converging module may be provided between the detection region and the photosensitive surface. That is, after the incident light passes through the detection region, the exit light exited from different exit positions pass through the converging module and are converged by the converging module to form the converged exit light. The photosensitive surface may acquire the light intensity value of the converged exit light.

According to embodiments of the present disclosure, the photosensitive surface may be designed to have a small area, so that the cost may be reduced, while the efficiency of the photosensitive surface receiving the exit light may not be greatly affected.

According to embodiments of the present disclosure, the device 1100 of detecting the living tissue element further includes a support module and a detection probe. The detection probe includes the M photosensitive surfaces. The support module is arranged on a target surface of the photosensitive surface or a target surface of the detection probe. Both the target surface of the photosensitive surface and the target surface of the detection probe refer to surfaces close to the detection region. The support module is used to support the converging module.

According to embodiments of the present disclosure, the converging module is arranged on the support module, so that the converging module may be fixed.

According to embodiments of the present disclosure, the converging module includes a convex lens or an annular lens. The annular lens includes a single annular lens, or the annular lens is formed by an arrangement of a plurality of convex lenses.

Figure 19:
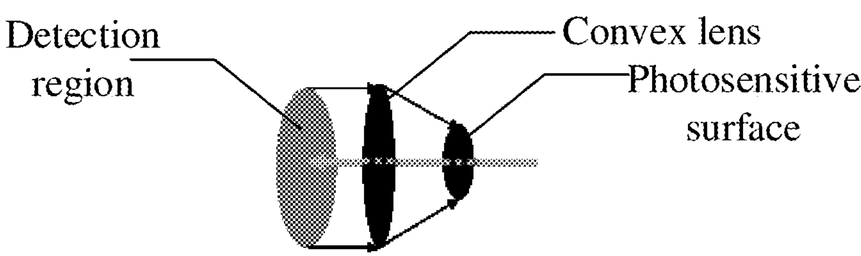
FIG. 19 schematically shows a schematic diagram of a combination of a convex lens and a circular photosensitive surface to achieve a light reception according to embodiments of the present disclosure.

According to embodiments of the present disclosure, the converging module may include a convex lens. With a combination of the convex lens and the photosensitive surface, it is possible to receive the light intensity value of the exit light of a large area exit region by using a photosensitive surface with a small effective area. Referring to FIG. 19, FIG. 19 schematically shows a schematic diagram of a combination of a convex lens and a circular photosensitive surface to achieve a light reception according to embodiments of the present disclosure.

Figure 20:
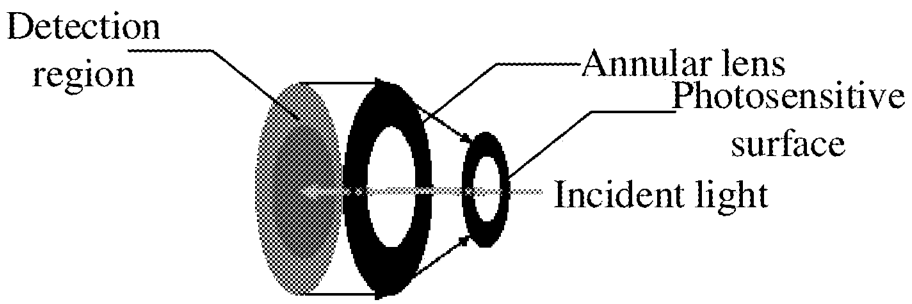
FIG. 20 schematically shows a schematic diagram of a combination of an annular lens and a ring photosensitive surface to achieve a light reception according to embodiments of the present disclosure.

The converging module may include an annular lens, and the annular lens may include a single annular lens. With a combination of the single annular lens and the photosensitive surface, a photosensitive surface with a small effective area may receive the light intensity value of the exit light of a large area exit region. Referring to FIG. 20, FIG. 20 schematically shows a schematic diagram of a combination of an annular lens and a ring photosensitive surface to achieve a light reception according to embodiments of the present disclosure.

Figure 21:
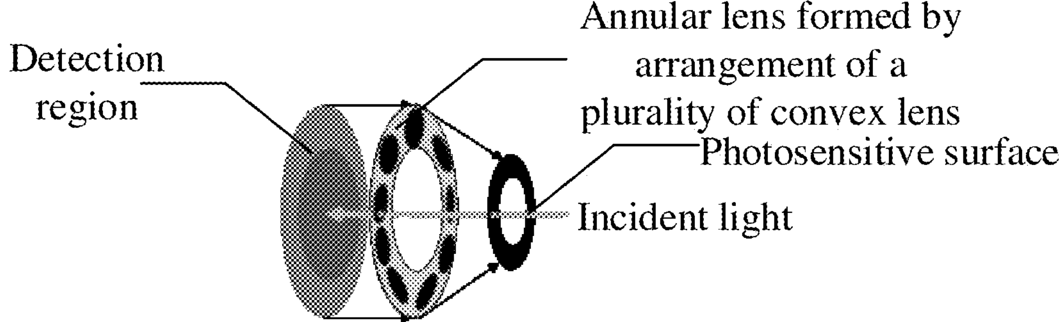
FIG. 21 schematically shows a schematic diagram of a combination of an annular lens formed by an arrangement of a plurality of convex lenses and a ring photosensitive surface to achieve a light reception according to embodiments of the present disclosure.
Figure 22:
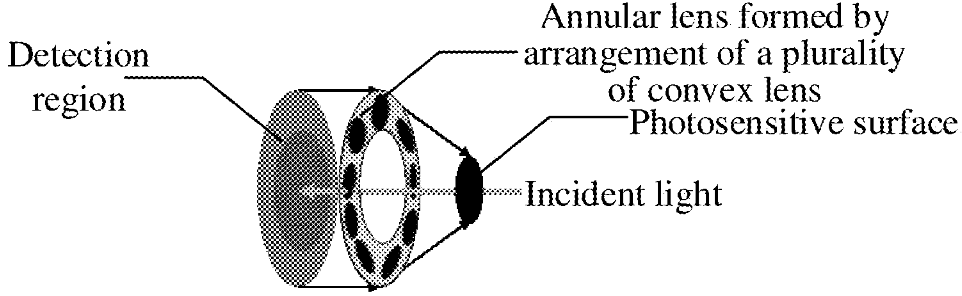
FIG. 22 schematically shows a schematic diagram of a combination of an annular lens formed by an arrangement of a plurality of convex lenses and a circular photosensitive surface to achieve a light reception according to embodiments of the present disclosure.

The converging module may include an annular lens, and the annular lens may be formed by an arrangement of a plurality of convex lenses. Referring to FIG. 21 and FIG. 22, FIG. 21 schematically shows a schematic diagram of a combination of an annular lens formed by an arrangement of a plurality of convex lenses and a ring photosensitive surface to achieve a light reception according to embodiments of the present disclosure, and FIG. 22 schematically shows a schematic diagram of a combination of an annular lens formed by an arrangement of a plurality of convex lenses and a circular photosensitive surface to achieve a light reception according to embodiments of the present disclosure. With the annular lens, light of an annular exit region may be received by a photosensitive surface with a common shape, such as a circular photosensitive surface or a square photosensitive surface.

According to embodiments of the present disclosure, surfaces of S photosensitive surfaces among the M photosensitive surfaces are respectively provided with filter films, where M≥2, M≥S. The filter film is used to allow the photosensitive surface to acquire the light intensity value of the exit light corresponding to the target wavelength. The target wavelength belongs to the plurality of predetermined wavelengths.

According to embodiments of the present disclosure, the surfaces of the S photosensitive surfaces among the M photosensitive surfaces are respectively provided with filter films for filtering out incident light having wavelengths other than the corresponding target wavelength. The target wavelength refers to a predetermined wavelength that may pass through the filter film. The target wavelength may include one or more target wavelengths. The photosensitive surface provided with the filter film may be referred to as a target photosensitive surface. Different target photosensitive surfaces may allow the same number or different numbers of predetermined wavelengths to pass through.

Exemplarily, there may be five predetermined wavelengths, including λ1, λ2, λ3, λ4 and λ5. M=S=4, and the four photosensitive surfaces include photosensitive surface 1, photosensitive surface 2, photosensitive surface 3, and photosensitive surface 4. The filter film arranged on the photosensitive surface 1 is used to pass through λ1 and λ3 and filter out λ2, λ4 and λ5. For the photosensitive surface 1, the target wavelengths may include λ1 and λ3.

The filter film arranged on the photosensitive surface 2 is used to pass through λ2 and filter out λ, λ3, λ4 and λ5. For the photosensitive surface 2, the target wavelength may include λ2.

The filter film arranged on the photosensitive surface 3 is used to pass through λ4 and filter out λ1, λ2, λ3 and λ5. For the photosensitive surface 3, the target wavelength may include λ4.

The filter film arranged on the photosensitive surface 4 is used to pass through λ5 and filter out λ1, λ2, λ3 and λ4. For the photosensitive surface 4, the target wavelength may include λ5.

Figure 23:
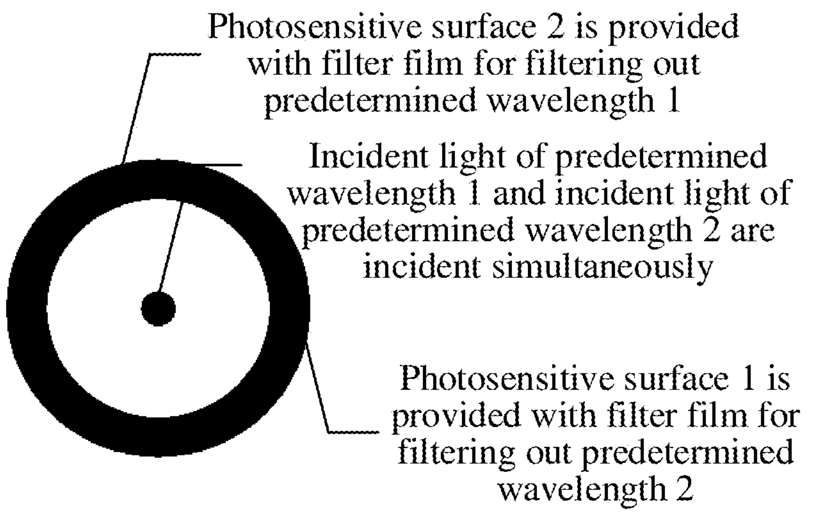
FIG. 23 schematically shows a schematic diagram of a combination of a ring photosensitive surface and a filter film to achieve a light reception according to embodiments of the present disclosure.
Figure 24:
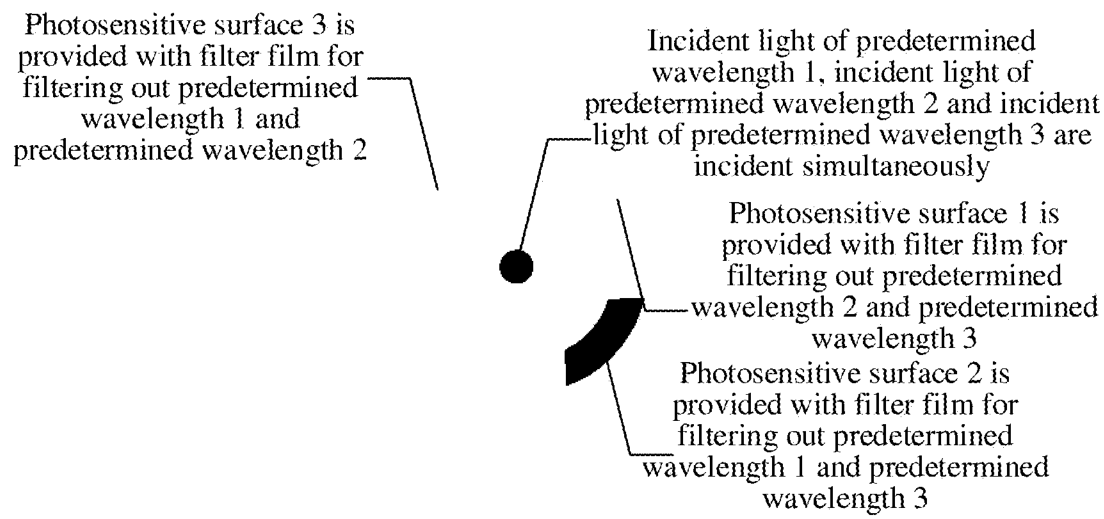
FIG. 24 schematically shows a schematic diagram of a combination of a sector-ring photosensitive surface and a filter film to achieve a light reception according to embodiments of the present disclosure.

A description will be given below with reference to FIG. 23 and FIG. 24. FIG. 23 schematically shows a schematic diagram of a combination of a ring photosensitive surface and a filter film to achieve a light reception according to embodiments of the present disclosure. FIG. 24 schematically shows a schematic diagram of a combination of a sector-ring photosensitive surface and a filter film to achieve a light reception according to embodiments of the present disclosure.

According to embodiments of the present disclosure, the device 1100 of detecting the living tissue element further includes a mask arranged on an initial photosensitive surface. A light transmittance of the mask is less than or equal to a light transmittance threshold. The mask is used to be provided on the initial photosensitive surface to obtain the photosensitive surface.

According to embodiments of the present disclosure, a shape of the mask is determined according to the shape of the jitter distribution of the exit light.

Figure 25:
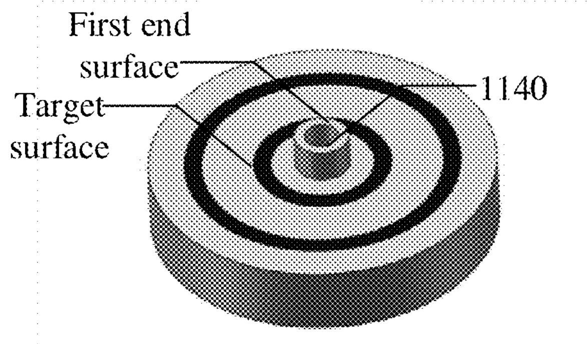
FIG. 25 schematically shows a schematic diagram of providing a first sleeve on a detection probe according to embodiments of the present disclosure.

As shown in FIG. 25, according to embodiments of the present disclosure, the device 1100 of detecting the living tissue element further includes a detection probe including the M photosensitive surfaces. The detection probe is provided with a first sleeve 1140. A first end surface of the first sleeve 1140 exceeds the target surface of the detection probe. The first end surface represents an end surface close to the detection region, and the target surface of the detection probe represents a surface close to the detection region.

According to embodiments of the present disclosure, in order to shield interference light, the first sleeve 1140 may be arranged on the detection probe so that the end surface of the first sleeve 1140 close to the detection region exceeds the target surface of the detection probe. The interference light may include surface-reflected light and/or diffracted light.

According to embodiments of the present disclosure, a second end surface and/or an inner region of the first sleeve 1140 are/is provided with a scattering object. The first end surface and the second end surface are two opposite end surfaces, and the inner region includes a partial inner region or an entire inner region.

According to embodiments of the present disclosure, in order to make the light spot irradiated with the incident light on the detection region have a uniform intensity distribution, it is possible to adopt a method of providing a scattering object at a corresponding part of the first sleeve. The scattering object may include sulfuric acid paper, silica gel, or a target mixture. The target mixture may include a mixture of polydimethylsiloxane and titanium dioxide particles.

Figure 26:
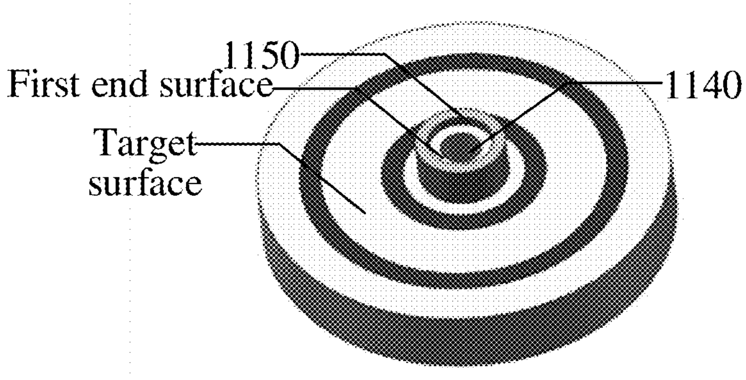
FIG. 26 schematically shows a schematic diagram of providing a second sleeve outside a target region of the first sleeve according to embodiments of the present disclosure.

As shown in FIG. 26, according to embodiments of the present disclosure, the device 1100 of detecting the living tissue element further includes a second sleeve 1150 arranged outside a target region of the first sleeve 1140. The target region represents a partial region or an entire region of the first sleeve 1140 exceeding the detection probe.

According to embodiments of the present disclosure, in order to make the light spot irradiated with the incident light on the detection region as large as possible, it is possible to adopt a method of arranging the second sleeve 1150 outside the target region of the first sleeve 1140.

According to embodiments of the present disclosure, the second sleeve 1150 is provided with a scattering object.

According to embodiments of the present disclosure, if the second sleeve 1150 is provided, it is possible to adopt a method of providing the scattering object at a corresponding part of the second sleeve 1150 in order to make the light spot irradiated with the incident light on the detection region have a uniform intensity distribution.

According to embodiments of the present disclosure, an inner diameter of the first sleeve 1140 is greater than or equal to an inner diameter threshold.

According to embodiments of the present disclosure, an opening of the first end surface of the first sleeve 1140 is greater than or equal to an opening of the second end surface of the first sleeve.

According to embodiments of the present disclosure, in order to make the light spot irradiated with the incident light on the detection region as large as possible, it is possible to design that the inner diameter of the first sleeve 1140 is greater than or equal to an inner diameter threshold, and/or the opening of the first end surface of the first sleeve 1140 is greater than or equal to the opening of the second end surface of the first sleeve, that is, the opening of the end surface of the first sleeve close to the detection region is greater than or equal to the opening of the end surface of the first sleeve away from the detection region.

Figure 28:
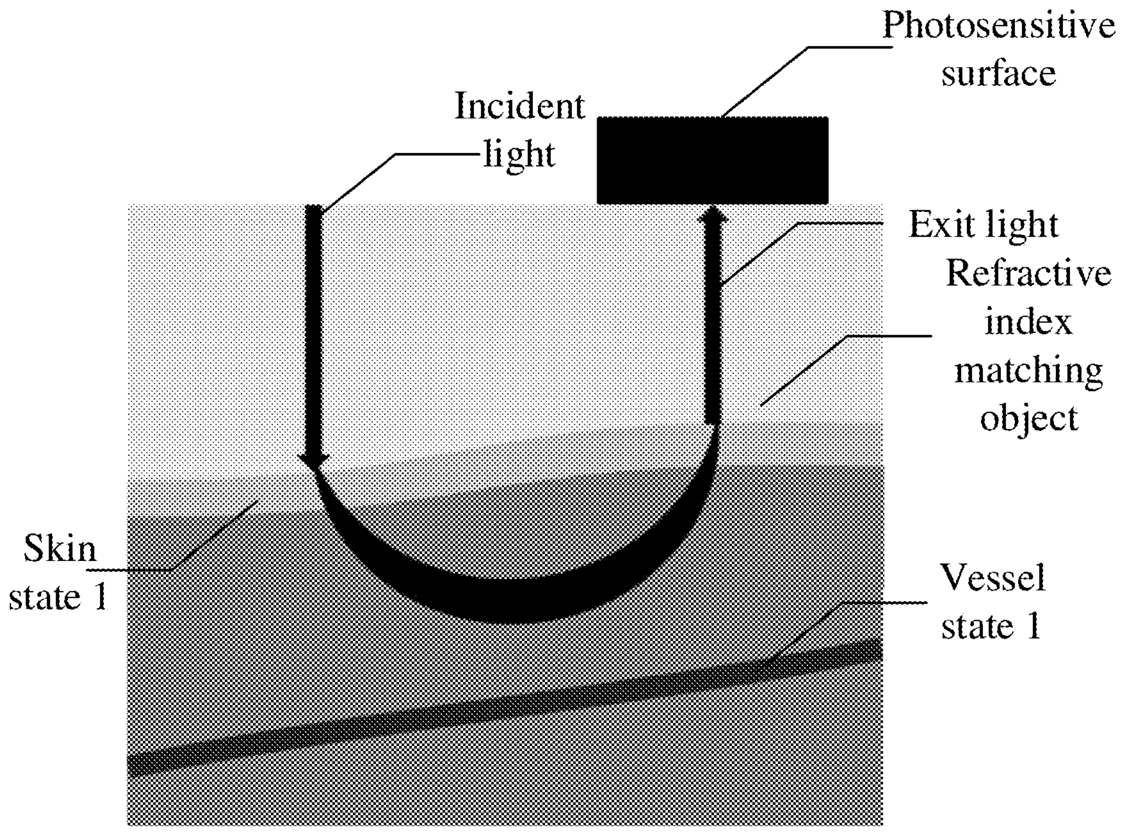
FIG. 28 schematically shows a schematic diagram of a photosensitive surface receiving exit light in a case of a refractive index matching object being filled according to embodiments of the present disclosure.

As shown in FIG. 28 to FIG. 29, according to embodiments of the present disclosure, a refractive index matching object is filled between the photosensitive surface and the detection region.

According to embodiments of the present disclosure, the jitter may cause an unstable surface of the detection region, and then cause a change in an exit angle of the exit light. Therefore, in order to minimize the adverse influences caused by the jitter, it is possible to fill a refractive index matching object between the photosensitive surface and the detection region to improve the stability and efficiency of the photosensitive surface receiving the exit light.

Figure 27:
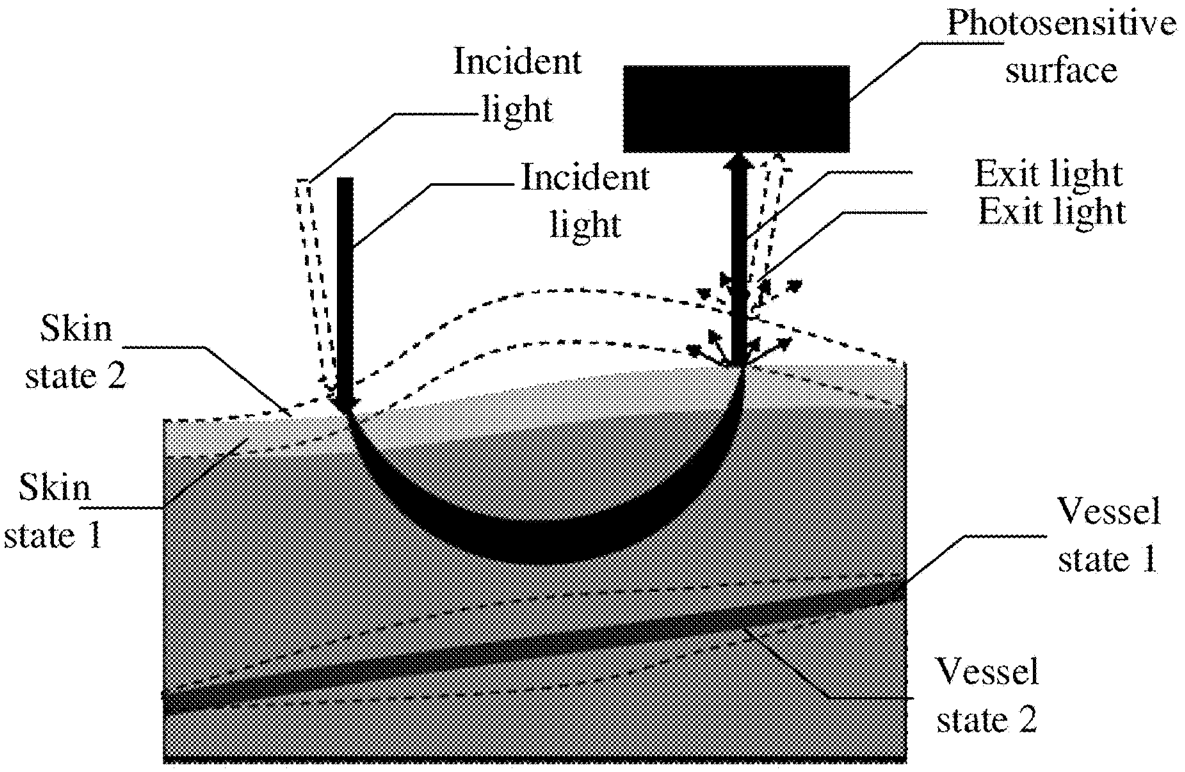
FIG. 27 schematically shows a schematic diagram of a photosensitive surface receiving exit light in a case of no refractive index matching object being filled according to embodiments of the present disclosure.

Illustratively, a description is given by taking a jitter caused by a pulse beat as an example. The pulse beat may be reflected by a blood vessel state. FIG. 27 schematically shows a schematic diagram of the photosensitive surface receiving the exit light in a case of no refractive index matching object being filled according to embodiments of the present disclosure. In FIG. 27, a blood vessel state 1 represents a vasoconstriction state, a blood vessel state 2 represents a vasodilation state, a skin state 1 represents a skin state corresponding to the blood vessel state 1, and a skin state 2 represents a skin state corresponding to the blood vessel state 2. As shown in FIG. 27, the jitter may cause an unstable skin surface at the detection region, and then cause a change in the exit angle of the exit light.

FIG. 28 schematically shows a schematic diagram of the photosensitive surface receiving the exit light in a case of a refractive index matching object being filled according to embodiments of the present disclosure.

FIG. 29 schematically shows another schematic diagram of the photosensitive surface receiving the exit light in a case of a refractive index matching object being filled according to embodiments of the present disclosure.

As shown in FIG. 28 and FIG. 29, the stability and efficiency of the photosensitive surface receiving the exit light may be improve by filling the refractive index matching object between the photosensitive surface and the detection region.

According to embodiments of the present disclosure, a shape of the incident light includes a point shape, a line shape, or a plane shape.

According to embodiments of the present disclosure, the plane shape may include a circle, a ring, a square, or a triangle, etc.

According to embodiments of the present disclosure, a positional relationship between the incident position and the M photosensitive surfaces includes one selected from: the M photosensitive surfaces being located inside all the incident positions, the M photosensitive surfaces being located outside all the incident positions, or the M photosensitive surfaces and the incident positions forming a nesting positional relationship.

According to embodiments of the present disclosure, the positional relationship between the incident positions and the M photosensitive surfaces may include one of the following cases, which will be described with reference to the accompanying drawings.

Figures 32, 33, 34, 35, 36:
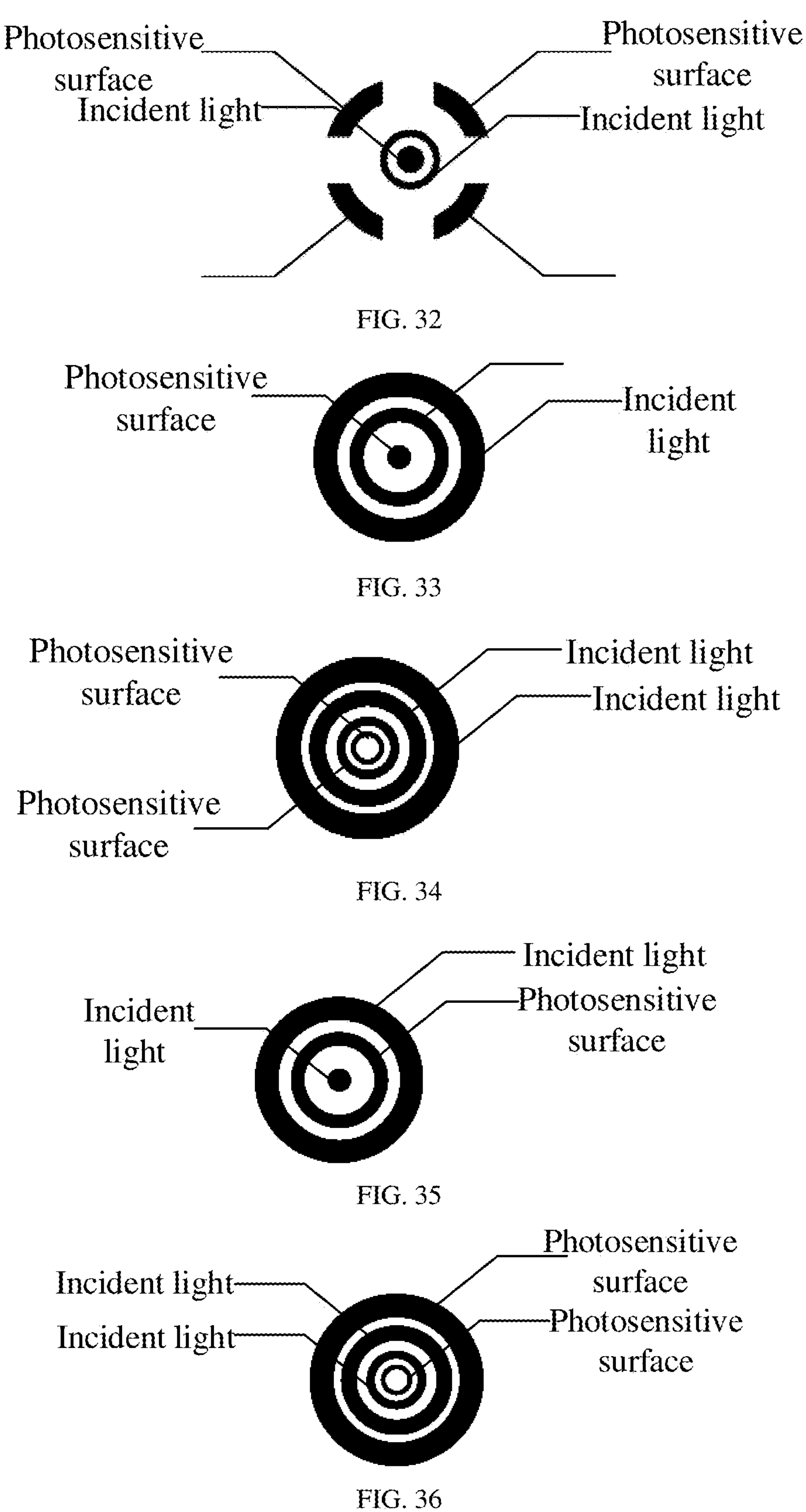
FIG. 32 schematically shows a schematic diagram of an incidence by circular incident light and ring incident light and a peripheral reception by a second set of photosensitive surfaces according to embodiments of the present disclosure.
FIG. 33 schematically shows a schematic diagram of a peripheral incidence by two ring incident light and an internal reception by a circular photosensitive surface according to embodiments of the present disclosure.
FIG. 34 schematically shows a schematic diagram of a peripheral incidence by two ring incident light and an internal reception by a third set of photosensitive surfaces according to embodiments of the present disclosure.
FIG. 35 schematically shows a schematic diagram of a nesting reception according to embodiments of the present disclosure.
FIG. 36 schematically shows a schematic diagram of another nesting reception according to embodiments of the present disclosure.

In a first case, the M photosensitive surfaces are all arranged at an outer periphery of all the incident positions. The above-mentioned arrangement of the positional relationship may form an implementation of a central incidence of incident light and a peripheral reception of light. Referring to FIG. 30 to FIG. 32, FIG. 30 shows a case of an incidence at a plurality of incident positions and a reception by one photosensitive surface, and FIG. 31 to FIG. 32 show cases of an incidence at a plurality of incident positions and a reception by a plurality of photosensitive surfaces.

FIG. 30 schematically shows a schematic diagram of an incidence by circular incident light and ring incident light and a peripheral reception by a ring photosensitive surface according to embodiments of the present disclosure.

FIG. 31 schematically shows a schematic diagram of an incidence by circular incident light and ring incident light and a peripheral reception by a first set of photosensitive surfaces according to embodiments of the present disclosure, where the first set of photosensitive surfaces includes two ring photosensitive surfaces. FIG. 32 schematically shows a schematic diagram of an incidence by circular incident light and ring incident light and a peripheral reception by a second set of photosensitive surfaces according to embodiments of the present disclosure, where the second set of photosensitive surfaces includes four sector-ring photosensitive surfaces.

In a second case, all the incident positions are arranged at an outer periphery of the M photosensitive surfaces, that is, the M photosensitive surfaces are surrounded by all the incident positions. The above-mentioned arrangement of the positional relationship may form an implementation of a peripheral incidence of light and a central reception of light. Referring to FIG. 33 to FIG. 34, FIG. 33 shows a case of an incidence at a plurality of incident positions and a reception by one photosensitive surface, and FIG. 34 shows a case of an incidence at a plurality of incident positions and a reception by a plurality of photosensitive surfaces.

FIG. 33 schematically shows a schematic diagram of a peripheral incidence by two ring incident light and an internal reception by a circular photosensitive surface according to embodiments of the present disclosure.

FIG. 34 schematically shows a schematic diagram of a peripheral incidence by two ring incident light and an internal reception by a third set of photosensitive surfaces according to embodiments of the present disclosure, where the third set of photosensitive surfaces includes two ring photosensitive surfaces.

Figure 37:
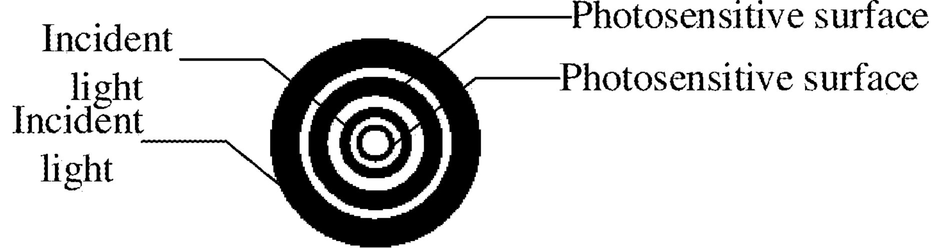
FIG. 37 schematically shows a schematic diagram of still another nesting reception according to embodiments of the present disclosure.

In a third case, W photosensitive surfaces of the M photosensitive surfaces are arranged at the outer periphery of a part of the incident positions and M-W photosensitive surfaces of the M photosensitive surfaces are arranged inside the other part of the incident positions, that is, the W photosensitive surfaces are arranged at the outer periphery of a part of the incident positions, and the M-W photosensitive surfaces are surrounded by the other part of the incident positions. The above-mentioned arrangement of the positional relationship may form an implementation of a nesting reception. Referring to FIG. 35 to FIG. 37, FIG. 35 shows a case of an incidence at a plurality of incident positions and a reception by one photosensitive surface, and FIG. 36 to FIG. 37 show cases of an incidence at a plurality of incident positions and a reception by a plurality of photosensitive surfaces.

FIG. 35 schematically shows a schematic diagram of a nesting reception according to embodiments of the present disclosure. In FIG. 35, a ring photosensitive surface is arranged between ring incident light and circular incident light.

FIG. 36 schematically shows a schematic diagram of another nesting reception according to embodiments of the present disclosure. FIG. 37 schematically shows a schematic diagram of still another nesting reception according to embodiments of the present disclosure.

According to embodiments of the present disclosure, the device 1100 of detecting the living tissue element further includes a protective portion. The protective portion is arranged on a target surface of the photosensitive surface and is used to protect the photosensitive surface. The target surface of the photosensitive surface refers to a surface close to the detection region.

According to embodiments of the present disclosure, in order to protect the photosensitive surface, a protective portion may be provided on the target surface of the photosensitive surface. The protective portion may be made of a transparent and flexible material. The protective portion may include an anti-reflection film or optical glass. A distance between the protective portion and the target surface of the photosensitive surface may be determined according to the material of the protective portion.

For example, if the protective portion is an anti-reflection film, a distance between the anti-reflection film and the target surface of the photosensitive surface may be zero. For another example, if the protective portion is optical glass, a distance between the optical glass and the target surface of the photosensitive surface is greater than or equal to a distance threshold. The distance threshold may be determined according to actual conditions.

Any number of the modules and units according to embodiments of the present disclosure, or at least part of functions of any number of them may be implemented in one module. Any one or more of the modules and units according to embodiments of the present disclosure may be split into a plurality of modules for implementation. Any one or more of the modules and units according to embodiments of the present disclosure may be implemented at least partially as a hardware circuit, such as a field programmable gate array (FPGA), a programmable logic array (PLA), a system on a chip, a system on a substrate, a system on a package, an application specific integrated circuit (ASIC), or may be implemented by hardware or firmware in any other rational manner of integrating or encapsulating the circuit, or may be implemented by any one of three implementation modes of software, hardware and firmware or an appropriate combination thereof. Alternatively, one or more of the modules and units according to embodiments of the present disclosure may be at least partially implemented as a computer program module that may performs the corresponding functions when executed.

For example, any number of the acquisition module and the processing module may be combined into one module/unit for implementation, or any one of the modules/units may be split into a plurality of modules/units. Alternatively, at least part of the functions of one or more of these modules/units may be combined with at least part of the functions of other modules/units and implemented in one module/unit. According to embodiments of the present disclosure, at least one of the acquisition module and the processing module may be implemented at least partially as a hardware circuit, such as a field programmable gate array (FPGA), a programmable logic array (PLA), a system on a chip, a system on a substrate, a system on a package, an application specific integrated circuit (ASIC), or may be implemented by hardware or firmware in any other rational manner of integrating or encapsulating the circuit, or may be implemented by any one of the three implementation modes of software, hardware and firmware or an appropriate combination thereof. Alternatively, at least one of the acquisition module and the processing module may be at least partially implemented as a computer program module that may perform the corresponding functions when executed.

It should be noted that the device of detecting the living tissue element in embodiments of the present disclosure corresponds to the description of the method of detecting the living tissue element in embodiments of the present disclosure. For the description of the device of detecting the living tissue element, reference may be specifically made to the description of the method of detecting the living tissue element, which will not be repeated here.

Figure 38:
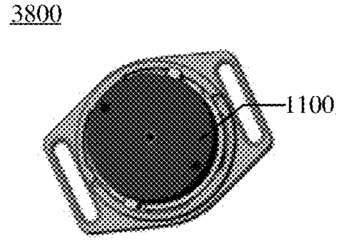
FIG. 38 schematically shows a schematic diagram of a wearable apparatus according to embodiments of the present disclosure.

FIG. 38 schematically shows a schematic diagram of a wearable apparatus according to embodiments of the present disclosure. A wearable apparatus 3800 shown in FIG. 38 is just an example, and should not impose any limitation on a function and a scope of use of the present disclosure.

As shown in FIG. 38, the wearable apparatus 3800 includes the device 1100 of detecting the living tissue element.

According to the technical solutions of embodiments of the present disclosure, the photosensitive surface may acquire the light intensity value of the exit light exited from the exit position within the corresponding predetermined anti-jitter range. In the photosensitive surface with the above characteristics, the ratio of the area capable of stably receiving the exit light of the photosensitive surface to the area of the photosensitive surface is increased, then the stability of receiving the exit light is improved, the adverse effect of the change in the intensity distribution of the exit light caused by the jitter may be reduced, so that the detection accuracy may be improved.

Figure 39:
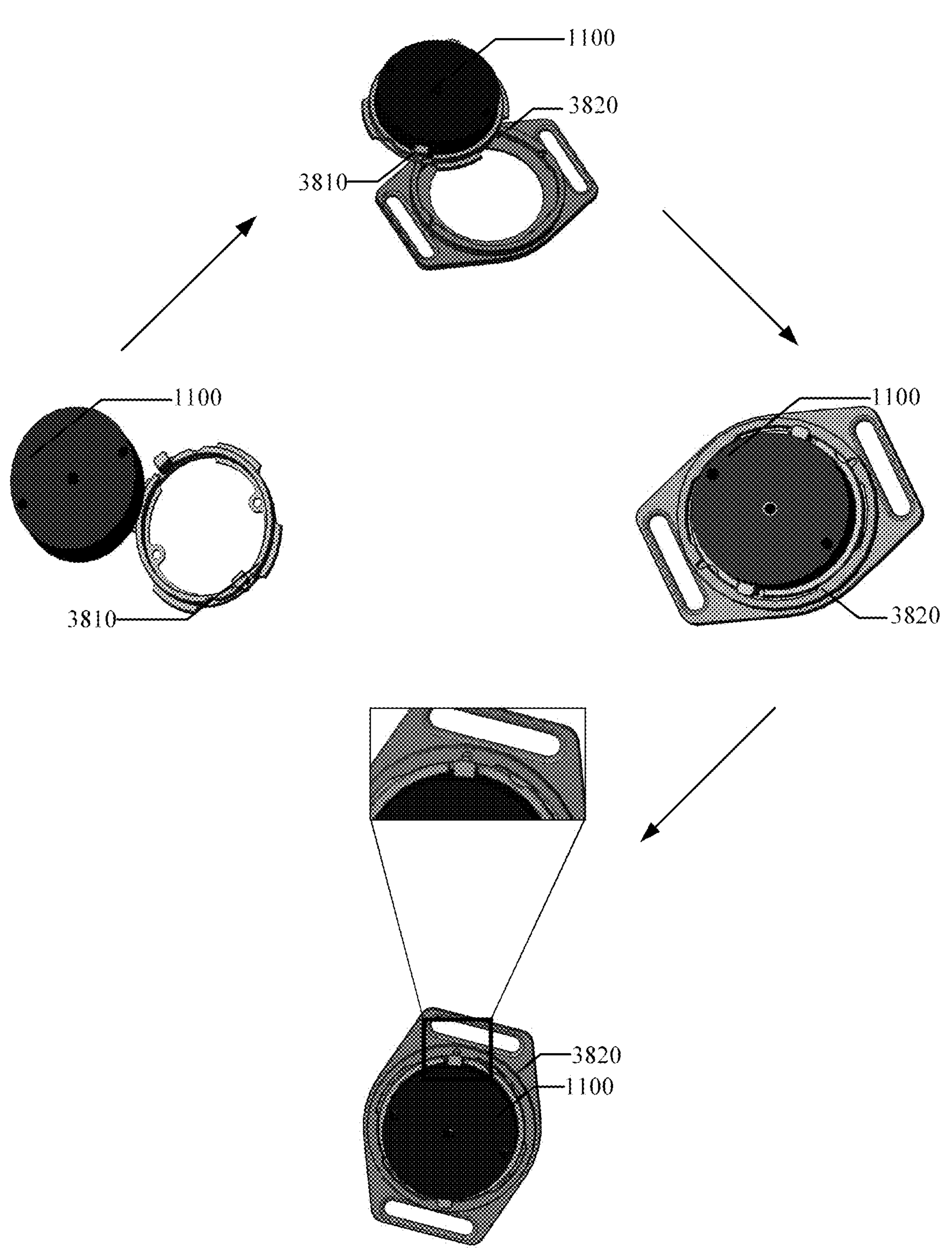
FIG. 39 schematically shows a schematic diagram of an assembly process of the wearable apparatus according to embodiments of the present disclosure.

As shown in FIG. 39, according to embodiments of the present disclosure, the wearable apparatus 3800 further includes a buckle portion 3810 and a body 3820. The buckle portion 3810 and the body 3820 are used to cooperate to fix the device 1100 of detecting the living tissue element.

According to embodiments of the present disclosure, FIG. 39 schematically shows a schematic diagram of an assembly process of the wearable apparatus according to embodiments of the present disclosure.

According to embodiments of the present disclosure, a mass of a wearable apparatus 3900 is less than or equal to a mass threshold, so that a movement pattern of the wearable apparatus 3900 is consistent with a skin jitter pattern at the detection region.

According to embodiments of the present disclosure, in order to improve the detection accuracy, the wearable apparatus 3900 may have a small mass, so that the wearable apparatus 3900 may follow the skin jitter at the detection region when the wearable apparatus 3900 is worn at a position corresponding to the detection region, that is, the movement pattern of the wearable apparatus 3900 may be consistent with the skin jitter pattern at the detection region, and then the average optical path of the exit light received by the detection probe may be maintained within the predetermined optical path range during the skin jitter process. The average optical path of the exit light received by the detection probe may be maintained within the predetermined optical path range during the skin jitter process of the detection region because a relative position of the detection probe on the detection region may be kept unchanged or substantially unchanged if the wearable apparatus 3900 may follow the skin jitter at the detection region, and then the detection probe may receive the exit light exited from a fixed exit position. The fixed exit position here means an exit position that remains unchanged or substantially unchanged relative to the detection region. Furthermore, during the skin jitter process of the detection region, the incident position of the incident light may remain unchanged or substantially unchanged relative to the detection region. In a case that the incident position of the incident light and the exit position of the exit light are determined, it is possible to ensure as much as possible that the average optical path of the exit light remains unchanged.

Figure 40:
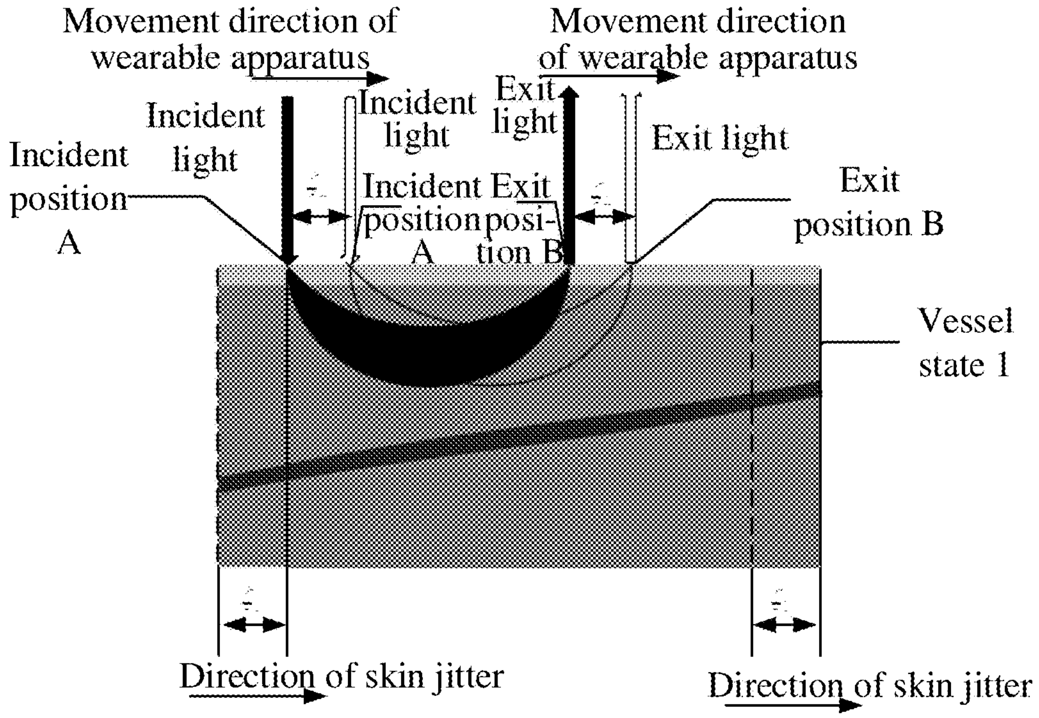
FIG. 40 schematically shows a schematic diagram of maintaining an average optical path of the exit light received by the detection probe within a predetermined optical path range during a skin jitter process in a case that the wearable apparatus is consistent with a skin jitter pattern according to embodiments of the present disclosure.

Exemplarily, FIG. 40 schematically shows a schematic diagram of maintaining the average optical path of the exit light received by the detection probe within a predetermined optical path range during a skin jitter process in a case that the wearable apparatus is consistent with a skin jitter pattern according to embodiments of the present disclosure. During the skin jitter process, the detection probe (not shown in FIG. 40) may stably receive the exit light that is exited from the exit position B on the detection region after the incident light is incident on the incident position A on the detection region. A movement amplitude of the skin is represented by $\zeta_1$, and a movement amplitude of the detection probe is represented by $\zeta_2$, $\zeta_1=\zeta_2$.

According to embodiments of the present disclosure, the wearable apparatus 3900 causes the movement amplitude of the skin at the detection region to be less than or equal to a movement amplitude threshold.

According to embodiments of the present disclosure, in order to improve the detection accuracy, the wearable apparatus 3900 may have a large mass, so that when the wearable apparatus 3900 is arranged at a position corresponding to the detection region, it may press the skin jitter at the detection region, that is, the movement amplitude of the skin at the detection region is less than or equal to a movement amplitude threshold, and then the average optical path of the exit light received by the detection probe may be maintained within a predetermined optical path range during the skin jitter process. The average optical path of the exit light received by the detection probe may be maintained within the predetermined optical path range during the skin jitter process at the detection region because a relative position of the detection probe on the detection region may be kept unchanged or substantially unchanged if the wearable apparatus 3900 may press the skin jitter at the detection region, and then the detection probe may receive the exit light exited from a fixed exit position. Furthermore, during the skin jitter process of the detection region, the incident position of the incident light may remain unchanged or substantially unchanged relative to the detection region. In a case that the incident position of the incident light and the exit position of the exit light are determined, it is possible to ensure as much as possible that the average optical path of the exit light remains unchanged.

Figure 41:
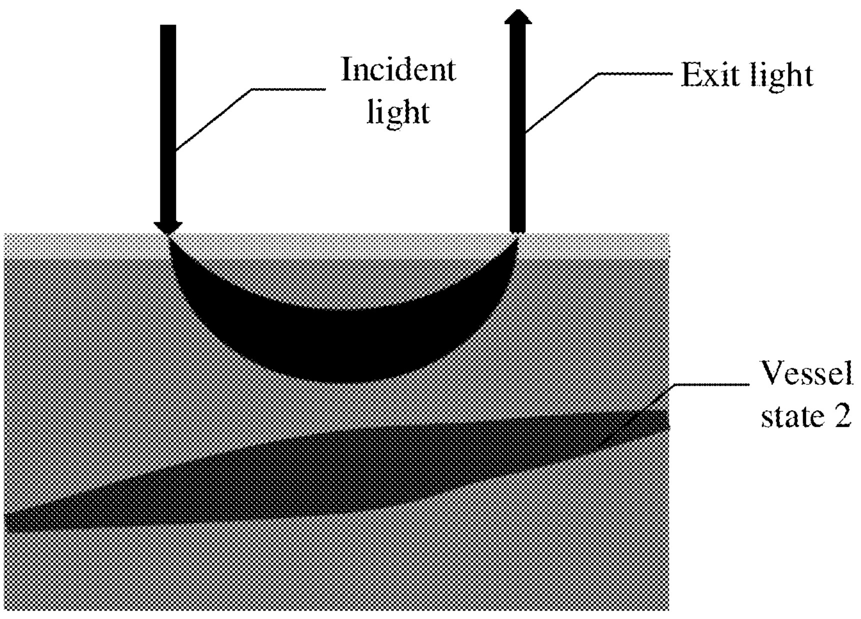
FIG. 41 schematically shows a schematic diagram of maintaining an average optical path of the exit light received by the detection probe within a predetermined optical path range during a skin jitter process in a case that the wearable apparatus causes a movement amplitude of a skin at the detection region to be less than or equal to a movement amplitude threshold according to embodiments of the present disclosure.

Exemplarily, FIG. 41 schematically shows a schematic diagram of maintaining the average optical path of the exit light received by the detection probe within a predetermined optical path range during a skin jitter process in a case that the wearable apparatus causes a movement amplitude of a skin at the detection region to be less than or equal to a movement amplitude threshold according to embodiments of the present disclosure. In FIG. 41, the movement amplitude of the skin at the detection region is close to zero.

According to embodiments of the present disclosure, for the specific description of the device of detecting the living tissue element, reference may be made to the corresponding part above, and details will not be repeated here. In addition, the device of detecting the living tissue element includes a processor which may perform various appropriate actions and processes according to a program stored in a read only memory (ROM) or a program loaded from a storage portion into a random access memory (RAM). The processor may include, for example, a general-purpose microprocessor (for example, CPU), an instruction set processor and/or a related chipset and/or a special-purpose microprocessor (for example, an application specific integrated circuit (ASIC)), and the like. The processor may further include an on-board memory for caching purposes. The processor may include a single processing unit or a plurality of processing units for performing different actions of the method flow according to embodiments of the present disclosure.

Various programs and data required for the operation of the device of detecting the living tissue element are stored in the RAM. The processor, the ROM and the RAM are connected to each other through a bus. The processor performs various operations of the method flow according to embodiments of the present disclosure by executing the programs in the ROM and/or the RAM. It should be noted that the program may also be stored in one or more memories other than the ROM and the RAM. The processor may also perform various operations of the method flow according to embodiments of the present disclosure by executing the programs stored in the one or more memories.

According to embodiments of the present disclosure, the wearable apparatus may further include an input/output (I/O) interface which is also connected to the bus. The wearable apparatus may further include one or more of the following components connected to the I/O interface: an input part including a keyboard, a mouse, etc.; an output part including a cathode ray tube (CRT), a liquid crystal display (LCD), etc. and a speaker, etc.; a storage part including a hard disk, etc.; and a communication part including a network interface card such as a LAN card, a modem, and the like. The communication part performs communication processing via a network such as the Internet. A drive is also connected to the I/O interface as required. A removable medium, such as a magnetic disk, an optical disk, a magneto-optical disk, a semiconductor memory, and the like, is installed on the drive as required, so that the computer program read therefrom is installed into the storage part.

The present disclosure further provides a computer-readable storage medium, which may be included in the apparatus/device/system described in the above embodiments; or exist alone without being assembled into the apparatus/device/system. The above-mentioned computer-readable storage medium carries one or more programs that perform the methods according to embodiments of the present disclosure when being executed.

According to embodiments of the present disclosure, the computer-readable storage medium may be a non-transitory computer-readable storage medium, for example, may include but not limited to: a portable computer disk, a hard disk, a random access memory (RAM), a read-only memory (ROM), an erasable programmable read-only memory (EPROM) or flash memory, a portable compact disk read-only memory (CD-ROM), an optical storage device, a magnetic storage device, or any suitable combination of the above. In the present disclosure, the computer-readable storage medium may be any tangible medium that contains or stores programs that may be used by or in combination with an instruction execution system, apparatus or device.

For example, according to embodiments of the present disclosure, the computer-readable storage medium may include the above-mentioned ROM and/or RAM and/or one or more memories other than the ROM and RAM.

Embodiments of the present disclosure further include a computer program product, which contains a computer program. The computer program contains program code for performing the method provided by embodiments of the present disclosure.

When the computer program is executed by the processor, the above-mentioned functions defined in the system/device of embodiments of the present disclosure are performed. According to embodiments of the present disclosure, the above-described systems, devices, modules, units, etc. may be implemented by computer program modules.

In an embodiment, the computer program may rely on a tangible storage medium such as an optical storage device and a magnetic storage device. In another embodiment, the computer program may also be transmitted and distributed in the form of signals on a network medium, downloaded and installed through the communication part, and/or installed from the removable medium. The program code contained in the computer program may be transmitted by any suitable medium, including but not limited to a wireless one, a wired one, or any suitable combination of the above.

According to embodiments of the present disclosure, the program code for executing the computer programs provided by embodiments of the present disclosure may be written in any combination of one or more programming languages. In particular, these computing programs may be implemented using high-level procedures and/or object-oriented programming languages, and/or assembly/machine languages. Programming languages include, but are not limited to, Java, C++, Python, "C" language or similar programming languages. The program code may be completely executed on the user computing apparatus, partially executed on the user device, partially executed on the remote computing apparatus, or completely executed on the remote computing apparatus or server. In a case of involving a remote computing apparatus, the remote computing apparatus may be connected to a user computing apparatus through any kind of network, including a local area network (LAN) or a wide area networks (WAN), or may be connected to an external computing apparatus (e.g., through the Internet using an Internet service provider).

The flowcharts and block diagrams in the accompanying drawings illustrate the possible architecture, functions, and operations of the system, method, and computer program product according to various embodiments of the present disclosure. In this regard, each block in the flowcharts or block diagrams may represent a part of a module, a program segment, or a code, which part includes one or more executable instructions for implementing the specified logical function. It should be further noted that, in some alternative implementations, the functions noted in the blocks may also occur in a different order from that noted in the accompanying drawings. For example, two blocks shown in succession may actually be executed substantially in parallel, or they may sometimes be executed in a reverse order, depending on the functions involved. It should be further noted that each block in the block diagrams or flowcharts, and the combination of blocks in the block diagrams or flowcharts, may be implemented by a dedicated hardware-based system that performs the specified functions or operations, or may be implemented by a combination of dedicated hardware and computer instructions. Those skilled in the art may understand that the various embodiments of the present disclosure and/or the features described in the claims may be combined in various ways, even if such combinations are not explicitly described in the present disclosure. In particular, the various embodiments of the present disclosure and/or the features described in the claims may be combined in various ways without departing from the spirit and teachings of the present disclosure. All these combinations fall within the scope of the present disclosure.

Embodiments of the present disclosure have been described above. However, these embodiments are for illustrative purposes only, and are not intended to limit the scope of the present disclosure. Although the various embodiments have been described separately above, this does not mean that measures in the respective embodiments may not be used in combination advantageously. The scope of the present disclosure is defined by the appended claims and their equivalents. Those skilled in the art may make various substitutions and modifications without departing from the scope of the present disclosure, and these substitutions and modifications should all fall within the scope of the present disclosure.

What is claimed is:

1. A method of detecting a living tissue element, comprising:

irradiating a detection region with incident light having at least one predetermined wavelength, wherein the incident light passes through the detection region to form at least one beam of exit light exited from at least one exit position, and the incident light is incident on at least two incident positions;

obtaining a light intensity value corresponding to each beam of the exit light acquired by M photosensitive surfaces, so as to obtain T output light intensities, wherein each of the T output light intensities is obtained by processing the light intensity value of the exit light acquired by one or more of the M photosensitive surfaces, and each of the M photosensitive surfaces is configured to acquire the light intensity value of the exit light exited from the exit position, a ratio of an area of each photosensitive surface to a circumference of the photosensitive surface is greater than or equal to a ratio threshold, the ratio threshold is greater than or equal to 0.04 mm, when the ratio threshold is greater than or equal to 0.04 mm, the larger the area of the photosensitive surface, the better an effect of suppressing a jitter caused by a change in an intensity distribution of a light spot irradiated with the incident light on the detection region, $1 \leq T \leq M$; and determining a concentration of at least one detected tissue element according to at least one output light intensity corresponding to the at least one predetermined wavelength.

2. The method according to claim 1, wherein a ratio of an average optical path of the exit light received by each photosensitive surface in a target tissue layer to a total optical path is greater than or equal to a ratio threshold, and the total optical path is a total distance that the exit light travels in the detection region.

3. The method according to claim 1, further comprising:

determining a total area of a homogeneous photosensitive surface according to a tissue structure feature in the detection region, wherein the homogeneous photosensitive surface comprises one or more photosensitive surfaces, and the homogeneous photosensitive surface is configured to output one output light intensity.

4. The method according to claim 1, wherein a distance between the photosensitive surface and the surface of the detection region is less than or equal to a first distance threshold, and an efficiency of the photosensitive surface receiving the exit light is greater than or equal to an efficiency threshold.

5. The method according to claim 1, wherein the determining a concentration of at least one detected tissue element according to at least one output light intensity corresponding to the at least one predetermined wavelength comprises one of:

in a case of determining the concentration of each detected tissue element in the at least one detected tissue element, for each predetermined wavelength in the plurality of predetermined wavelengths, determining a first output light intensity and a second output light intensity from at least two output light intensities corresponding to the predetermined wavelength; and determining the concentration of the detected tissue element according to the first output light intensity and the second output light intensity corresponding to each predetermined wavelength, in a case of determining the concentration of each detected tissue element in the at least one detected tissue element, for each predetermine wavelength in the at least one predetermined wavelength, determining a third output light intensity from the at least one output light intensity corresponding to the predetermined wavelength; performing a differential processing on the third output light intensities corresponding to different predetermined wavelengths, so as to obtain at least one differential signal; and determining the concentration of the detected tissue element according to the at least one differential signal, in a case of determining the concentration of each detected tissue element in the at least one detected tissue element, for each predetermine wavelength in the at least one predetermined wavelength, determining at least one superimposed light intensity corresponding to the predetermined wavelength, wherein the superimposed light intensity is obtained by adding a plurality of output light intensities corresponding to the predetermined wavelength; and determining the concentration of the detected tissue element according to at least one superimposed light intensity corresponding to each predetermined wavelength, and in a case of determining the concentration of each detected tissue element in the at least one detected tissue element, for each predetermine wavelength in the at least one predetermined wavelength, determining a fourth output light intensity from the at least one output light intensity corresponding to the predetermined wavelength; and determining the concentration of the detected tissue element according to the fourth output light intensity corresponding to each predetermined wavelength.

6. The method according to claim 5, wherein the determining the concentration of the detected tissue element according to the first output light intensity and the second output light intensity corresponding to each predetermined wavelength comprises:

performing a differential processing on the first output light intensity and the second output light intensity corresponding to the predetermined wavelength, so as to obtain a differential signal; and determining the concentration of the detected tissue element according to the differential signal corresponding to each predetermined wavelength.

7. The method according to claim 5, wherein the first output light intensity and the second output light intensity are acquired at different time instants by a homogeneous photosensitive surface, the first output light intensity is a light intensity in a systole, the second output light intensity is a light intensity in a diastole, the homogeneous photosensitive surface comprises one or more photosensitive surfaces, a photosensitive surface corresponding to the first output light intensity is the same as or different from a photosensitive surface corresponding to the second output light intensity, and the homogeneous photosensitive surface is configured to output one output light intensity.

8. The method according to claim 5, wherein the first output light intensity corresponding to the predetermined wavelength is acquired by a first homogeneous photosensitive surface corresponding to the predetermined wavelength, the second output light intensity corresponding to the predetermined wavelength is acquired by a second homogeneous photosensitive surface corresponding to the predetermined wavelength, the first homogeneous photosensitive surface comprises one or more photosensitive surfaces, and the second homogeneous photosensitive surface comprises one or more photosensitive surfaces.

9. The method according to claim 8, wherein an average optical path of the exit light received at different photosensitive positions of each photosensitive surface in the first homogeneous photosensitive surface is within a first average optical path range, the first average optical path range is determined according to a first optical path mean value, and the first optical path mean value is a mean value calculated according to the average optical paths of the exit light received at the photosensitive positions of the first homogeneous photosensitive surface; and wherein an average optical path of the exit light received at different photosensitive positions of each photosensitive surface in the second homogeneous photosensitive surface is within a second average optical path range, the second average optical path range is determined according to a second optical path mean value, and the second optical path mean value is a mean value calculated according to the average optical paths of the exit light received at the photosensitive positions of the second homogeneous photosensitive surface, wherein an absolute value of a difference between the first optical path mean value and the second optical path mean value is within a first optical path difference range.

10. The method according to claim 5, wherein the determining the concentration of the detected tissue element according to the differential signal corresponding to each predetermined wavelength comprises:

performing a direct differential operation on the differential signals corresponding to different predetermined wavelengths, so as to obtain at least one wavelength differential signal; and determining the concentration of the detected tissue element according to the at least one wavelength differential signal.

11. The method according to claim 5, wherein the fourth output light intensity corresponding to the predetermined wavelength is acquired by the homogeneous photosensitive surface corresponding to the predetermined wavelength, and a difference between the average optical path of the exit light received at different photosensitive positions of each photosensitive surface in the homogeneous photosensitive surface and an optimal optical path corresponding to the predetermined wavelength is within a second optical path difference range.

12. The method according to claim 1, wherein each photosensitive surface comprises a ring photosensitive surface or a non-ring photosensitive surface, and different photosensitive surfaces have the same or different shapes, wherein the homogeneous photosensitive surface comprises the ring photosensitive surface or the non-ring photosensitive surface, the homogeneous photosensitive surface comprises one or more photosensitive surfaces, and the homogeneous photosensitive surface is configured to output one output light intensity.

13. The method according to claim 12, wherein the homogeneous photosensitive surface being the ring photosensitive surface comprises:

the homogeneous photosensitive surface comprises one photosensitive surface, and the homogeneous photosensitive surface is an independent ring photosensitive surface; or the homogeneous photosensitive surface comprises a plurality of photosensitive surfaces, and the homogeneous photosensitive surface is a ring photosensitive surface formed by combining the plurality of photosensitive surfaces; and wherein the homogeneous photosensitive surface being the non-ring photosensitive surface comprises:

the homogeneous photosensitive surface comprises one photosensitive surface, and the homogeneous photosensitive surface is an independent non-ring photosensitive surface; or the homogeneous photosensitive surface comprises a plurality of photosensitive surfaces, and the homogeneous photosensitive surface is a non-ring photosensitive surface formed by combining the plurality of photosensitive surfaces.

14. The method according to claim 13, wherein the homogeneous photosensitive surface comprises the ring photosensitive surface, a sector-ring photosensitive surface, a sector photosensitive surface, a circular photosensitive surface or a square photosensitive surface when it is determined that a distance between the homogeneous photosensitive surface and a target site is greater than or equal to a second distance threshold, wherein a shape of the homogeneous photosensitive surface is determined according to a jitter distribution of the exit light when it is determined that a distance between the homogeneous photosensitive surface and a target site is less than or equal to a third distance threshold.

15. The method according to claim 14, wherein the jitter distribution of the exit light is decomposed into a jitter distribution in a first direction and a jitter distribution in a second direction perpendicular to the first direction, a ratio of a length of the homogeneous photosensitive surface in the first direction to a length of the homogeneous photosensitive surface in the second direction is determined according to a ratio of a jitter amplitude of the exit light in the first direction to a jitter amplitude of the exit light in the second direction, and the exit light has a maximum jitter amplitude in the first direction.

16. The method according to claim 15, wherein the homogeneous photosensitive surface comprises a rectangular photosensitive surface or an elliptical photosensitive surface, a ratio of a length to a width of the rectangular photosensitive surface is determined according to the ratio of the jitter amplitude of the exit light in the first direction to the jitter amplitude of the exit light in the second direction, and a ratio of a major axis to a minor axis of the elliptical photosensitive surface is determined according to the ratio of the jitter amplitude of the exit light in the first direction to the jitter amplitude of the exit light in the second direction.

17. The method according to claim 1, wherein the light spot irradiated with the incident light on the detection region has a uniform intensity distribution.

18. The method according to claim 1, wherein an area of the light spot irradiated with the incident light on the detection region is greater than or equal to a light spot area threshold.

19. A device of detecting a living tissue element, comprising:

a light source module configured to irradiate a detection region by incident light having at least one predetermined wavelength, wherein the incident light passes through the detection region to form at least one beam of exit light exited from at least one exit position, and the incident light is incident on at least two incident positions;

an acquisition module comprising M photosensitive surfaces, wherein each of the M photosensitive surfaces is configured to acquire the light intensity value of the exit light exited from the exit position, the acquisition module is configured to obtain a light intensity value corresponding to each beam of the exit light acquired by the M photosensitive surfaces, so as to obtain T output light intensities, and each of the T output light intensities is obtained by processing the light intensity value of the exit light acquired by one or more of the M photosensitive surfaces, a ratio of an area of each photosensitive surface to a circumference of the photosensitive surface is greater than or equal to a ratio threshold, the ratio threshold is greater than or equal to 0.04 mm, when the ratio threshold is greater than or equal to 0.04 mm, the larger the area of the photosensitive surface, the better an effect of suppressing a jitter caused by a change in an intensity distribution of a light spot irradiated with the incident light on the detection region; and a processing module configured to determine a concentration of at least one detected tissue element according to at least one output light intensity corresponding to the at least one predetermined wavelength.

20. The device according to claim 19, wherein an included angle between each part of the photosensitive surface and a direction of the corresponding incident light is greater than or equal to 0° and less than or equal to 360°.

21. The device according to claim 19, wherein surfaces of S photosensitive surfaces in the M photosensitive surfaces are respectively provided with filter films, where M≥2, M≥S; and wherein the filter film is configured to allow the photosensitive surface to acquire the light intensity value of the exit light corresponding to a target wavelength, and the target wavelength belongs to the plurality of predetermined wavelengths.

22. The device according to claim 19, further comprising a detection probe, wherein the detection probe comprises the M photosensitive surfaces, and the detection probe is provided with a first sleeve; and wherein a first end surface of the first sleeve exceeds a target surface of the detection probe, the first end surface is an end surface close to the detection region, and the target surface of the detection probe is a surface close to the detection region.

23. The device according to claim 22, wherein a second end surface and/or an inner region of the first sleeve are/is provided with a scattering object, the first end surface and the second end surface are opposite end surfaces, and the inner region comprises a partial inner region or an entire inner region.

24. The device according to claim 22, further comprising a second sleeve outside a target region of the first sleeve, wherein the target region represents a partial region or an entire region of the first sleeve exceeding the target surface of the detection probe.

25. The device according to claim 22, wherein an opening of the first end surface of the first sleeve is greater than or equal to an opening of the second end surface of the first sleeve.

26. The device according to claim 19, wherein a refractive index matching object is filled between the photosensitive surface and the detection region.

27. A wearable apparatus, comprising the device of detecting the living tissue element according to claim 19.

28. The wearable apparatus according to claim 27, wherein a mass of the wearable apparatus is less than or equal to a mass threshold, so that a movement pattern of the wearable apparatus is consistent with a skin jitter pattern at the detection region.

29. The wearable apparatus according to claim 27, wherein the wearable apparatus causes a movement amplitude of a skin at the detection region to be less than or equal to a movement amplitude threshold.

* * * * *